US010898590B2

(12) United States Patent
Kim et al.

(10) Patent No.: US 10,898,590 B2
(45) Date of Patent: Jan. 26, 2021

(54) METHOD FOR DELIVERY OF BIOLOGICAL MOLECULE TO NERVOUS TISSUE

(71) Applicant: KOLON LIFE SCIENCE, INC., Gwacheon-si (KR)

(72) Inventors: Sujeong Kim, Seoul (KR); Heonsik Choi, Seoul (KR); Kyoungbaek Choi, Incheon (KR); Minjung Kim, Seoul (KR); Yejin Kwon, Seoul (KR); Hyeonyoul Lee, Ansan-si (KR); Minju Kim, Seoul (KR); Daewook Kim, Yongin-si (KR); Jangjoon Park, Seoul (KR); Yeomoon Sim, Seoul (KR)

(73) Assignee: KOLON LIFE SCIENCE, INC., Seoul (KR)

( * ) Notice: Subject to any disclaimer, the term of this patent is extended or adjusted under 35 U.S.C. 154(b) by 0 days.

(21) Appl. No.: 16/217,962

(22) Filed: Dec. 12, 2018

(65) Prior Publication Data

US 2019/0099504 A1 Apr. 4, 2019

Related U.S. Application Data

(63) Continuation-in-part of application No. 15/754,849, filed as application No. PCT/KR2016/010480 on Sep. 20, 2016.

(30) Foreign Application Priority Data

Sep. 21, 2015 (KR) ........................ 10-2015-0133349

(51) Int. Cl.
*A61P 25/04* (2006.01)
*A61K 48/00* (2006.01)
*A61K 9/00* (2006.01)
*C12N 15/86* (2006.01)
*A61K 38/20* (2006.01)
*A61K 38/51* (2006.01)

(52) U.S. Cl.
CPC ........ *A61K 48/0075* (2013.01); *A61K 9/0085* (2013.01); *A61K 38/2026* (2013.01); *A61K 38/2066* (2013.01); *A61K 38/51* (2013.01); *A61K 48/005* (2013.01); *A61P 25/04* (2018.01); *C12N 15/86* (2013.01); *C12Y 401/01015* (2013.01); *C12N 2710/10343* (2013.01); *C12N 2750/14143* (2013.01)

(58) Field of Classification Search
None
See application file for complete search history.

(56) References Cited

U.S. PATENT DOCUMENTS

| 6,436,908 B1 * | 8/2002 | Koch ..................... A61K 31/70 424/93.2 |
| 2008/0019969 A1 * | 1/2008 | Gorman ............. A61K 31/4164 424/141.1 |

FOREIGN PATENT DOCUMENTS

| EP | 1 621 208 A1 | 2/2006 |
| EP | 2 258 841 A1 | 12/2010 |
| KR | 10-2008-0007968 A | 1/2008 |

OTHER PUBLICATIONS

Jean-Marc G Guedon et al., "Current gene therapy using viral vectors for chronic pain", Molecular Pain, 2015, pp. 1-23, vol. 11, No. 27.
D Wolfe et al., "A human trial of HSV-mediated gene transfer for the treatment of chronic pain", Gene Therapy, 2009, pp. 455-460, vol. 16.
Darren Wolfe, PhD, et al., "A Clinical Trial of Gene Therapy for Chronic Pain", Pain Medicine, 2009, pp. 1325-1330, vol. 10, No. 7.
International Searching Authority, International Search Report for PCT/KR2016/010480 dated Jan. 11, 2017.
Denes B. et al., "Autoantigens Plus Interleukin-10 Suppress Diabetes Autoimmunity," Diabetes Technology & Therapeutics, Aug. 2010, vol. 12, No. 8, pp. 649-661 (19 pages).
Intellectual Property Office of Singapore, Communication dated Sep. 14, 2018, issued in corresponding Singaporean Application No. 11201802292U.
Denes, B. et al., "Durable Multicomponent Vaccine Suppression of Diabetes Autoimmunity", Molecular Therapy, 2009, vol. 17, Supplement 1, p. S67, Abstract 170, 1 page.
Weiss, K. et al., "Herpes simplex virus-based gene therapies for chronic pain", Journal of Pain and Palliative Care Pharmacotherapy, 2012, vol. 26, No. 3, pp. 291-293, 4 pages.
Srinivasan, R. et al.,"HSV vectors for gene therapy of chronic pain", Current Opinion in Molecular Therapeutics, 2008, vol. 10, No. 5, pp. 449-455, 7 pages.
Australian Patent Office; Communication dated Oct. 18, 2018 issued in corresponding Application No. 2016327213.
Kim et al., "AAV-GAS gene for rat models of neuropathic pain and Parkinson's disease", Acta Neurochirurgica, Supplement, vol. 101, 2008, pp. 99-105 (7 pages total).

(Continued)

Primary Examiner — Kimberly Chong
(74) Attorney, Agent, or Firm — Sughrue Mion, PLLC

(57) ABSTRACT

A method for delivery of a therapeutic agent to a nervous tissue. In particular, a method of delivering a therapeutic agent to a nervous tissue protected by the brain-blood barrier or meninges is disclosed. The method for delivery allows delivery of a therapeutic agent to a nervous tissue with high efficiency. In addition, the delivery method of a therapeutic agent to a nervous tissue is safe since it has lower side effects such as nervous damage than a method of administering a therapeutic agent directly to a nervous tissue.

10 Claims, 14 Drawing Sheets

Specification includes a Sequence Listing.

(56) References Cited

OTHER PUBLICATIONS

Erin D. Milligan et al., "Controlling pathological pain by adenovirally driven spinal production of the anti-inflammatory cytokine, interleukin-10", European Journal of Neuroscience, vol. 21, pp. 2136-2148, 2005, 13 pages total.

Jean-Philippe Vit et al., "Adenovector GAD65 gene delivery into the rat trigeminal ganglion produces orofacial analgesia", Molecular Pain, vol. 5, No. 1, Aug. 2009, 11 pages total.

Bela Denes et al., "Suppression of Hyperglycemia in NOD Mice After Inoculation With Recombinant Vaccinia Viruses", Molecular Biotechnology, vol. 34, No. 3, Nov. 2006, pp. 317-327, 11 pages total.

Sofie Robert et al., "Oral Delivery of Glutamic Acid Decarboxylase (GAD)-65 and IL10 by *Lactococcus lactis* Reverses Diabetes in Recent-Onset NOD Mice", Diabetes, vol. 63, Aug. 2014, pp. 2876-2887, 12 pages total.

European Patent Office; Communication dated Mar. 11, 2019 issued in counterpart European Application No. 16848886.4.

Milligan et al., "Repeated intrathecal injections of plasmid DNA encoding interleukin-10 produce prolonged reversal of neuropathic pain", Pain, 2006, vol. 126, pp. 294-308 (total 15 pages).

Liu et al., "Release of GABA from sensory neurons transduced with a GAD67-expressing vector occurs by non-vesicular mechanisms", Brain Research, 2005, pp. 297-304 (total 8 pages).

Kanao et al., "Gene Transfer of Glutamic Acid Decarboxylase 67 by Herpes Simplex Virus Vectors Suppresses Neuropathic Pain Induced by Human Immunodeficiency Virus gp120 Combined with ddC in Rats", Anesthesia & Analgesia, Jun. 2015, vol. 120, No. 6, pp. 1394-1404 (total 11 pages).

Song et al., "Construction and identification of eukaryotic expression vector containing GAD65 fragment and IL-10 gene", Chin Med Biotechnol, 2007, vol. 2, No. 2, pp. 105-109 (5 pages total).

* cited by examiner

[Fig. 1]
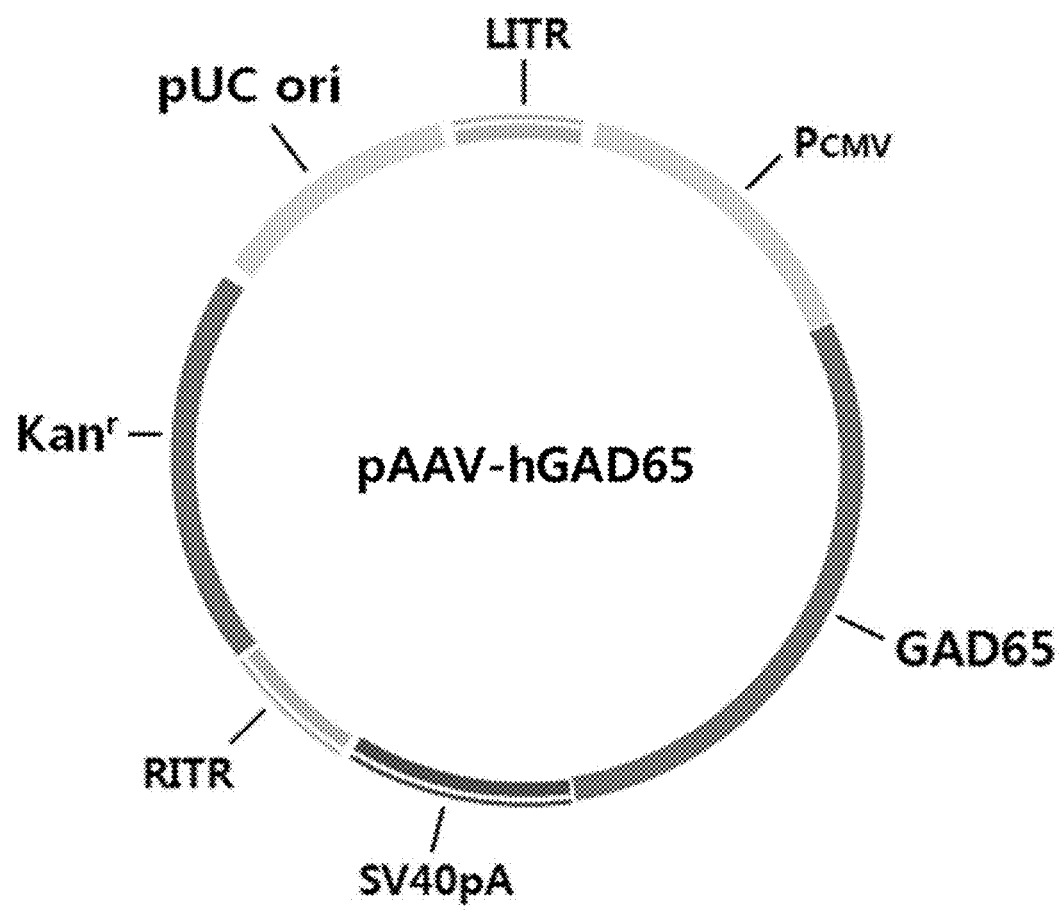

[Fig. 2]
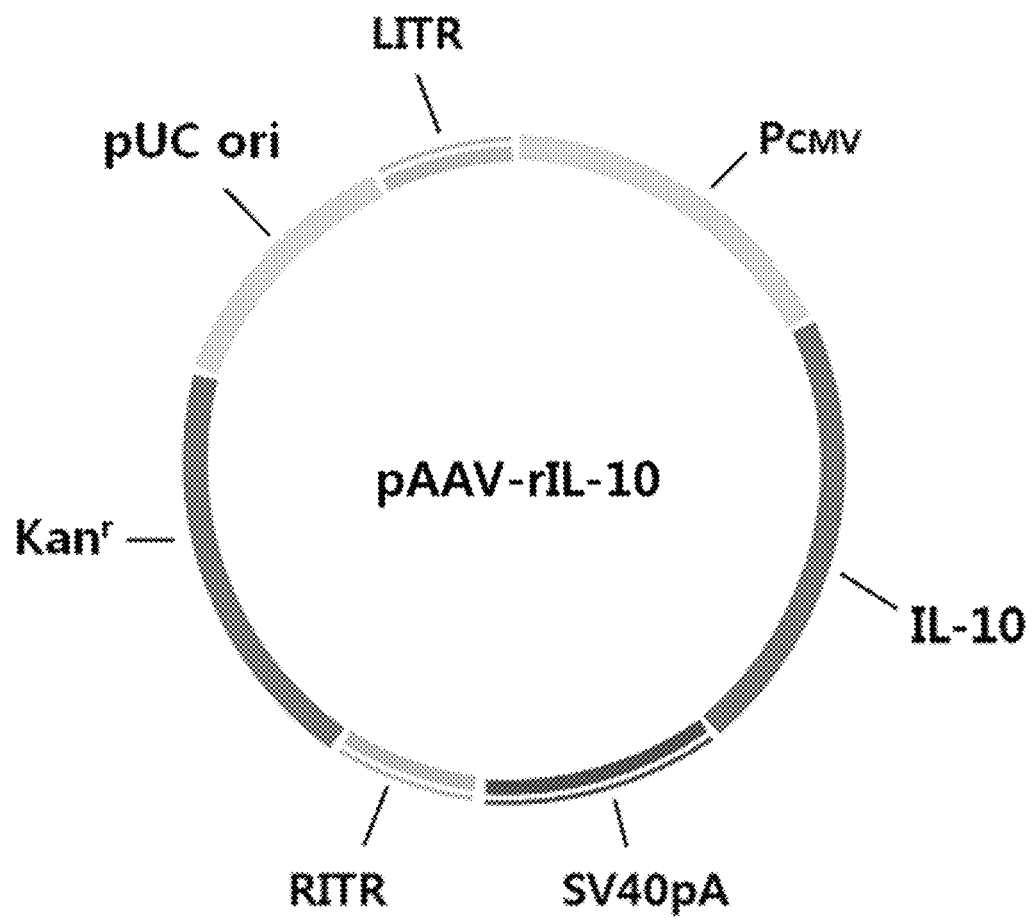

[Fig. 3]
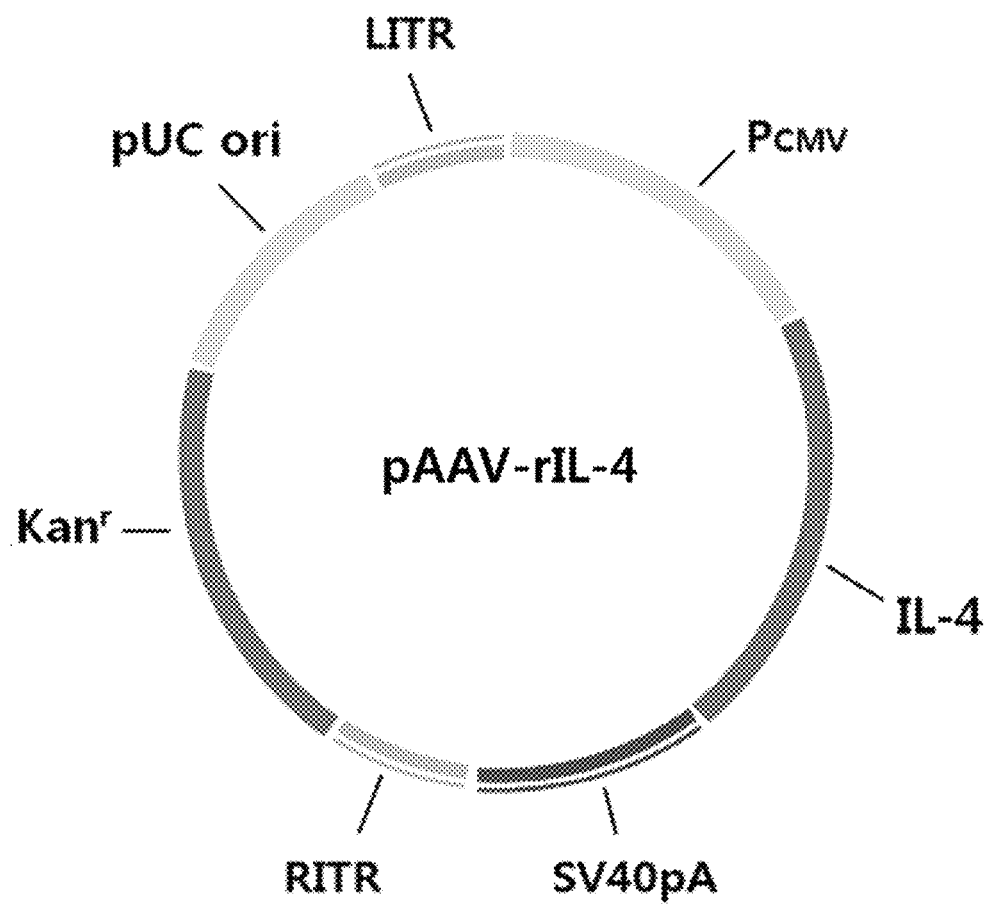

[Fig. 4]
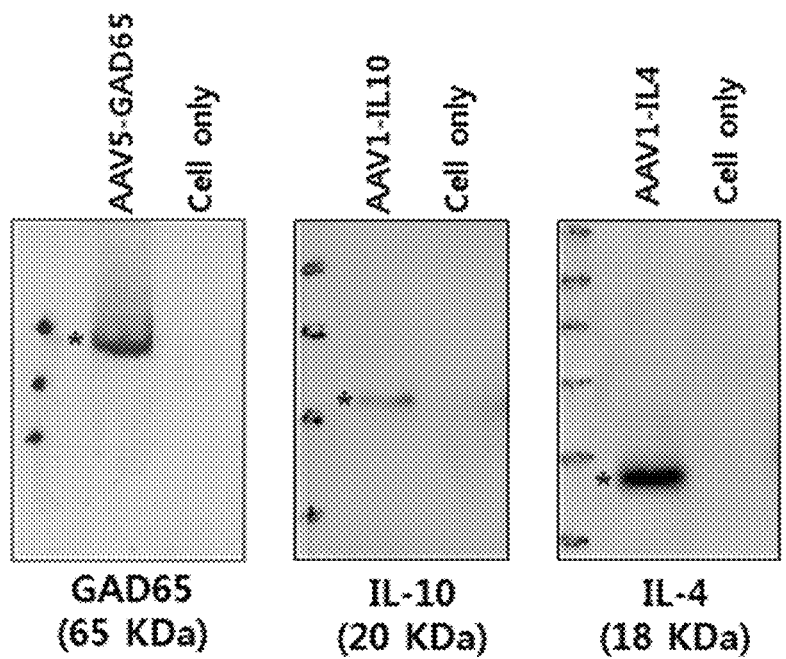
[Fig. 5]
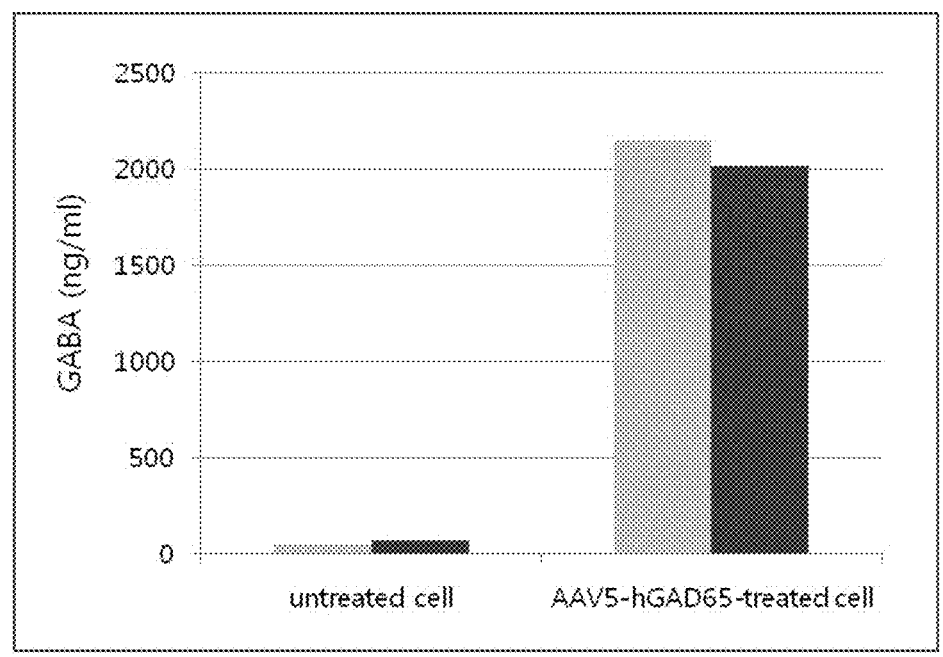

[Fig. 6]
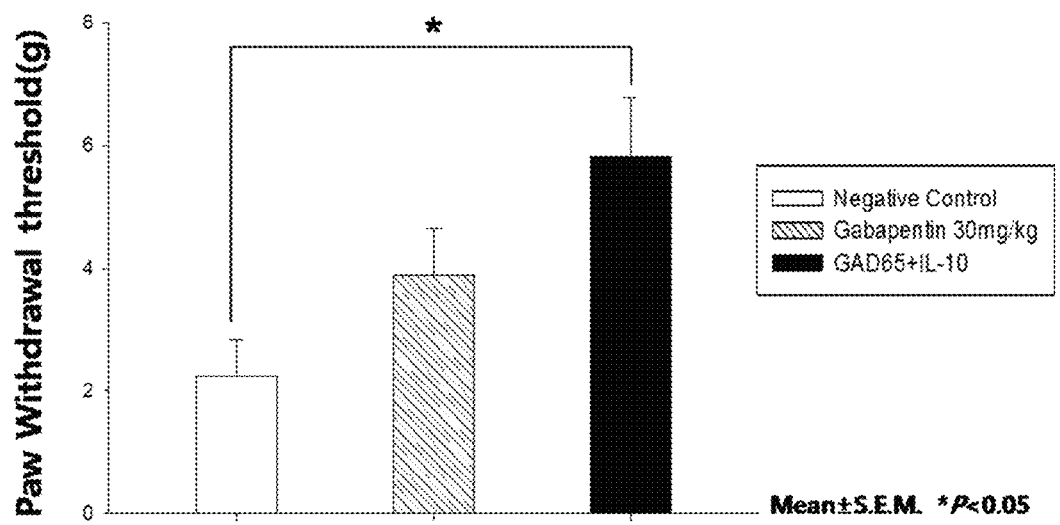
[Fig. 7]
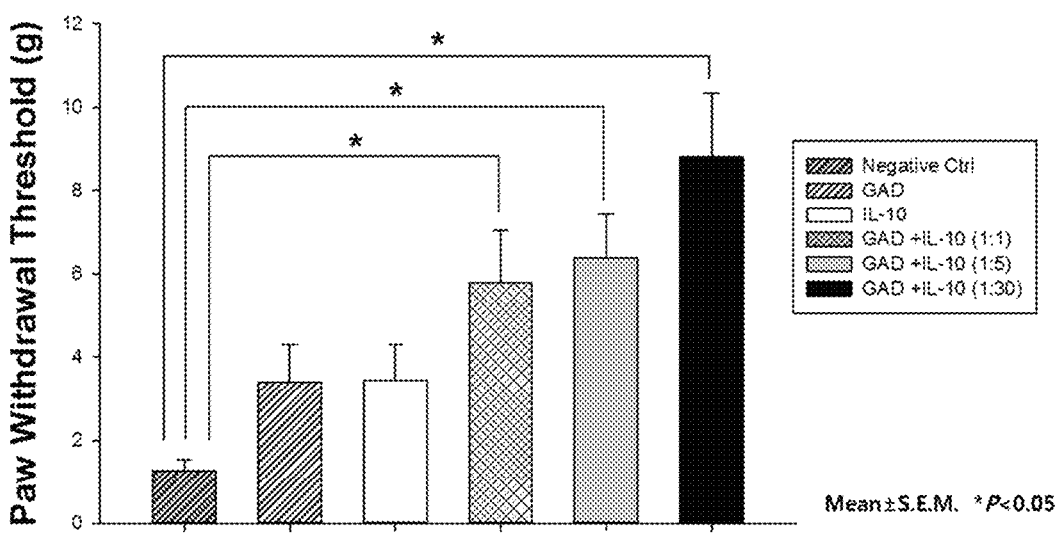

【Fig. 8】
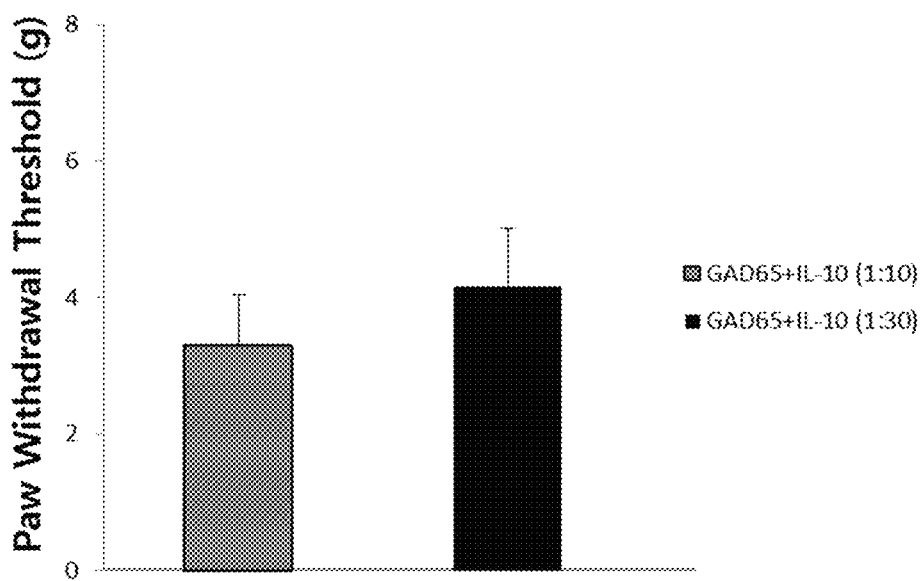
【Fig. 9】
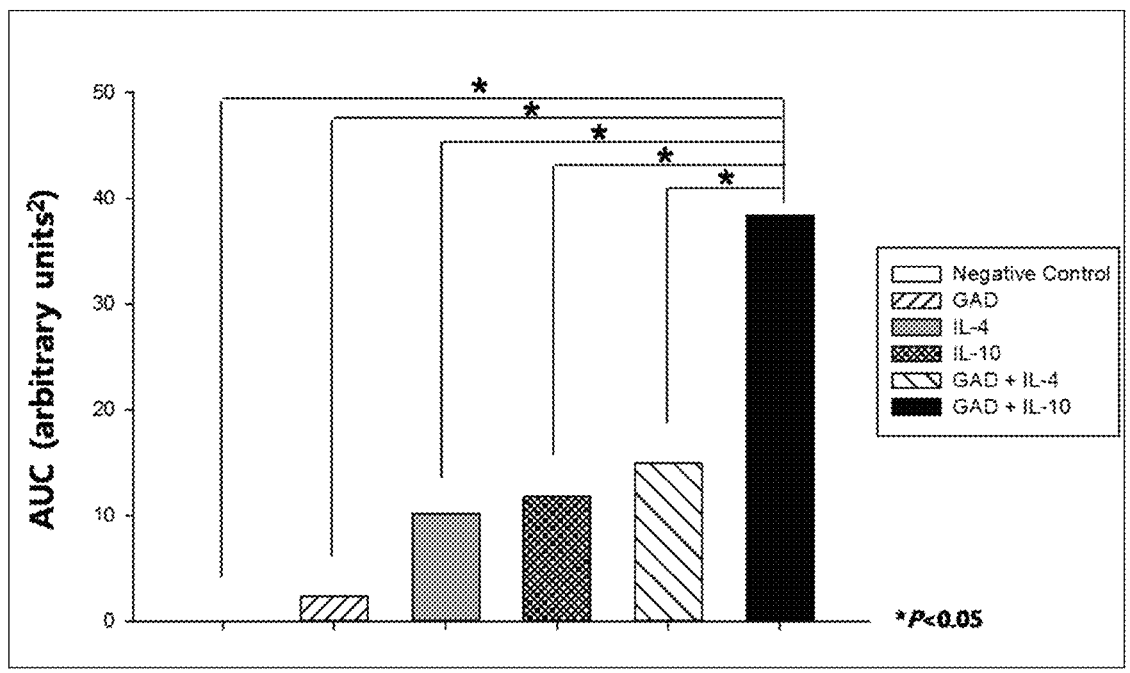

[Fig. 10A]
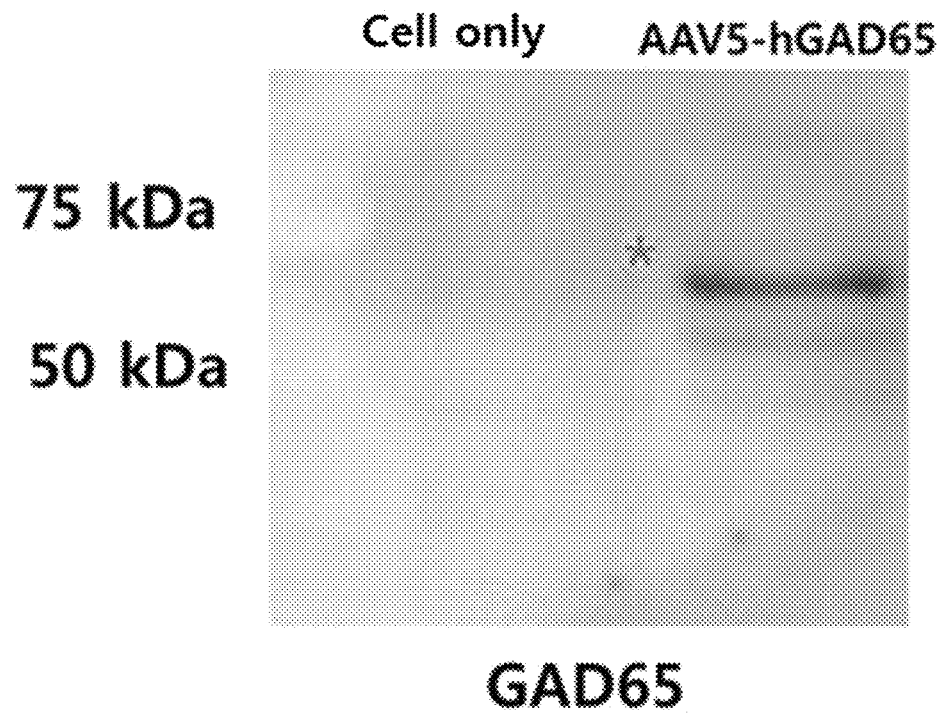
[Fig. 10B]
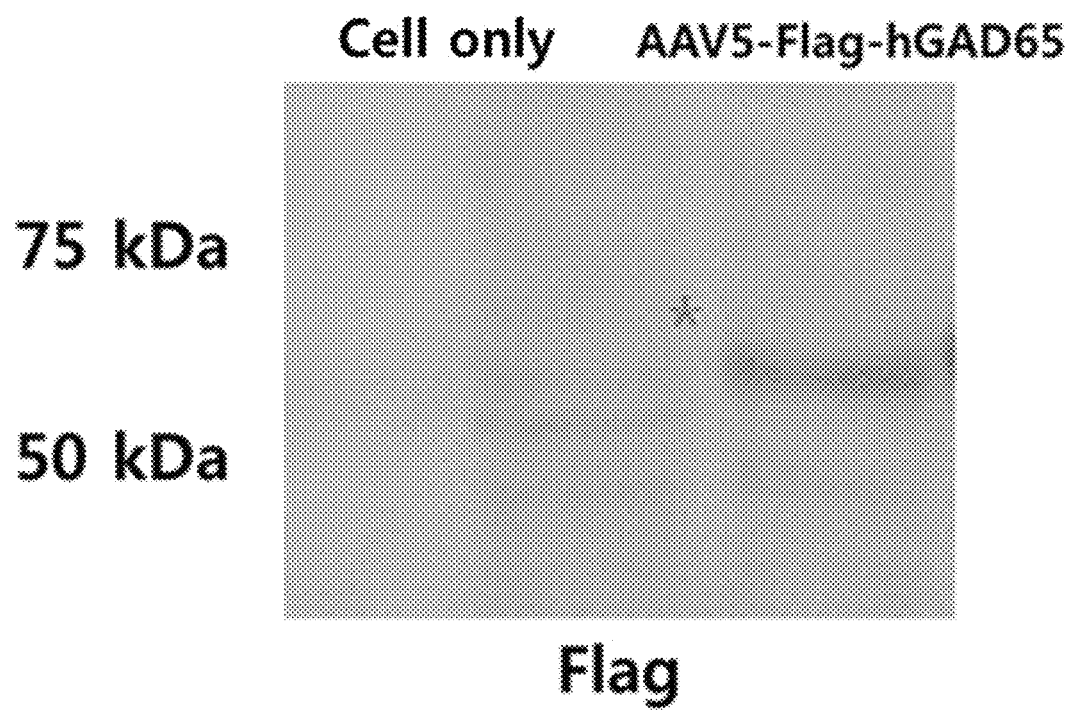

[Fig. 10C]
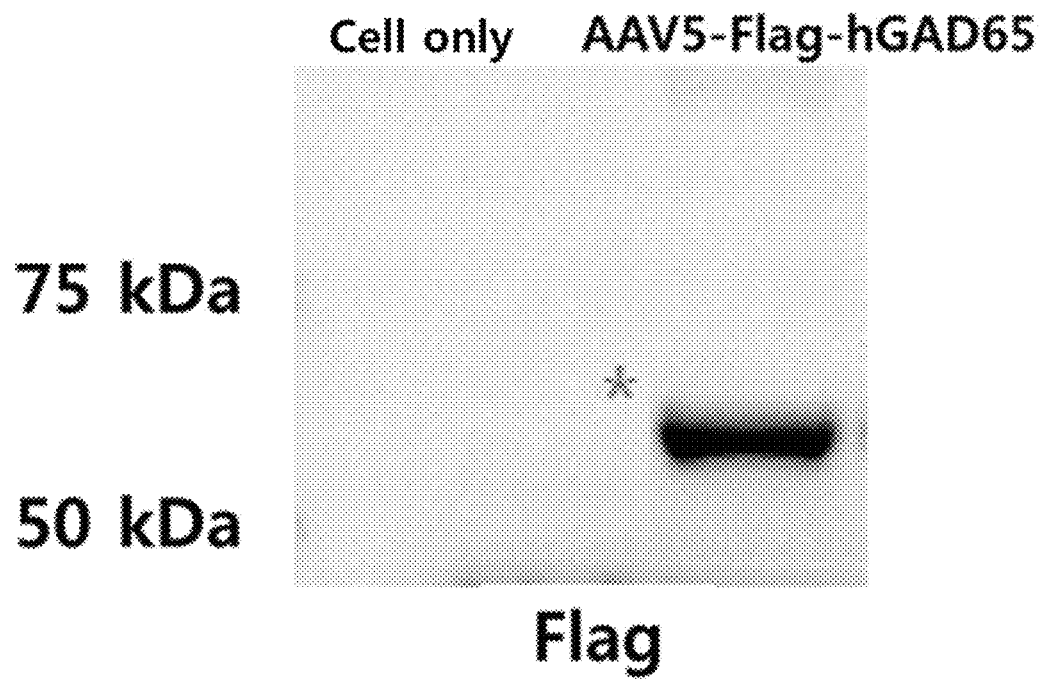
[Fig. 10D]
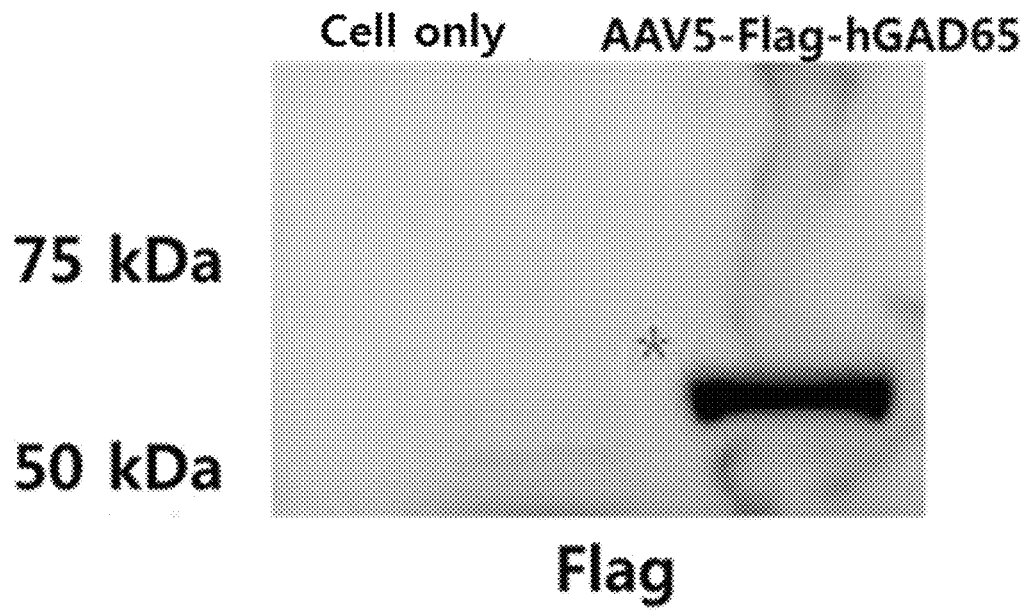

[Fig. 10E]
|  | Transgene expression level ||
|---|---|---|
|  | IL10 (ng/mL) | GDNF (ng/mL) |
| AAV5-GDNF/IL-10 | 1682 | 11.7 |
| AAV5-GDNF/IL-10 | 50.8 | 2.6 |
[Fig. 11]
Cell only        pAAV-GFP
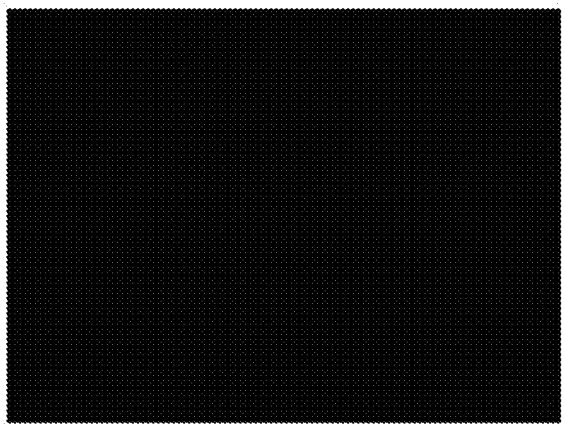
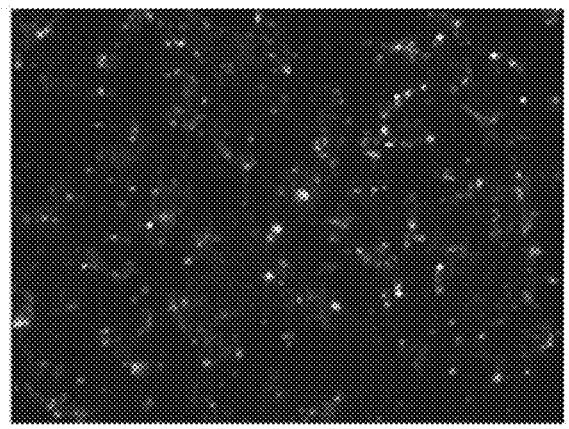

[Fig. 12]
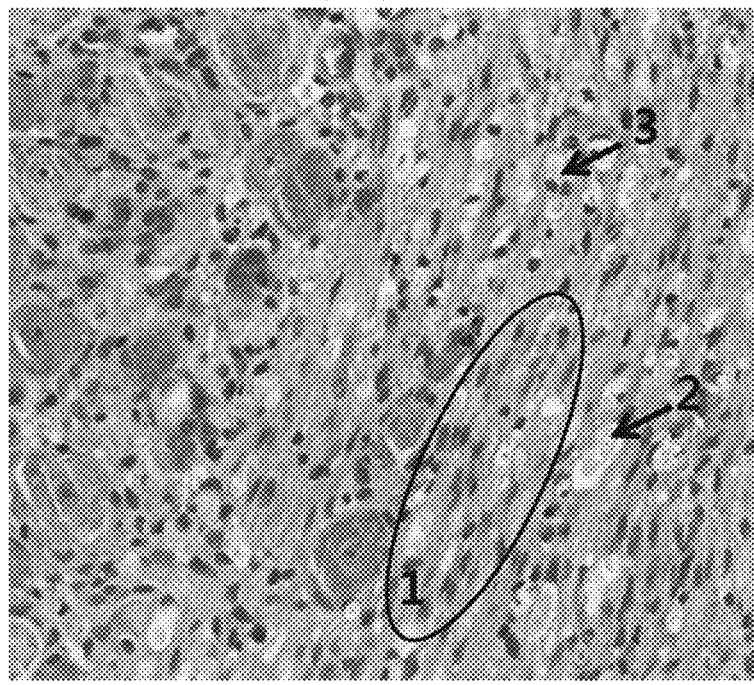

[Fig. 13A]
IHC: 4 weeks after transforaminal epidural injection
Dorsal root ganglion (DRG), X200
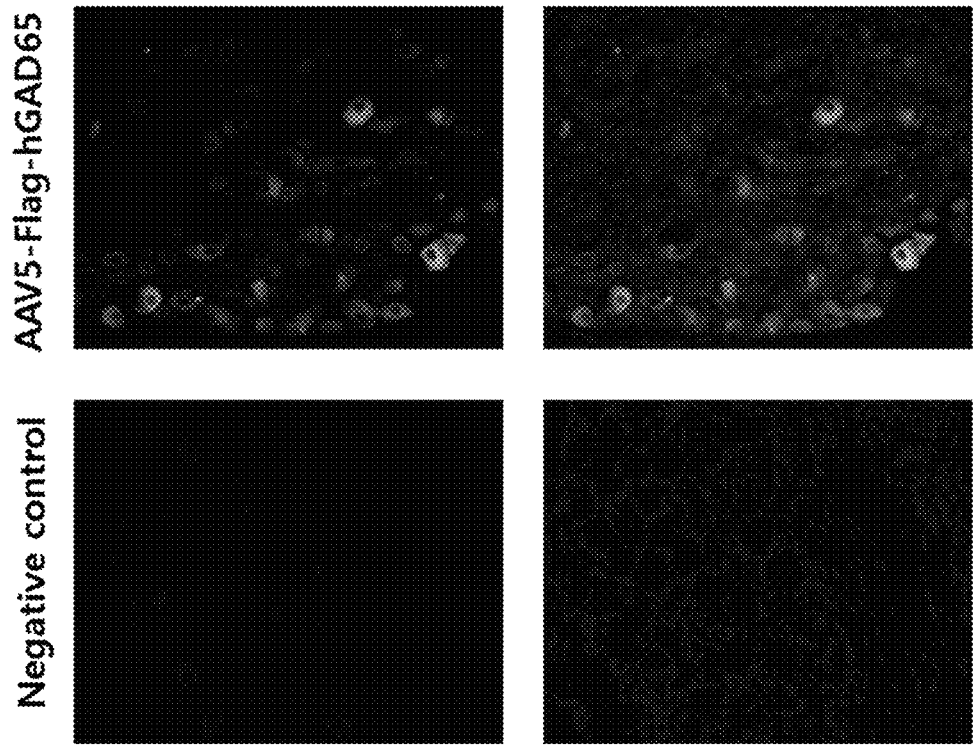
[Fig. 13B]
H&E: Transforaminal epidural injection
Dorsal root ganglion (DRG), X400
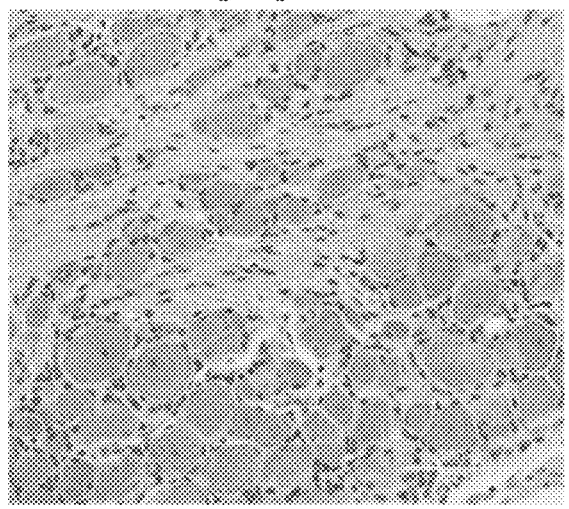
Abnormal findings: None

[Fig. 14]
IHC: 1 day after transforaminal epidural injection
Dorsal root ganglion (DRG), X200
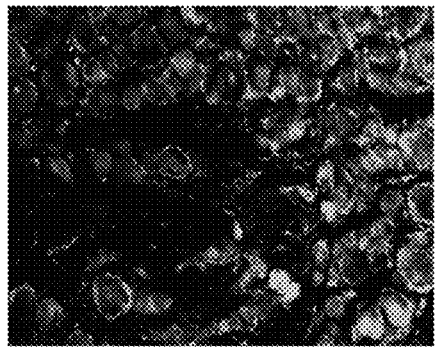
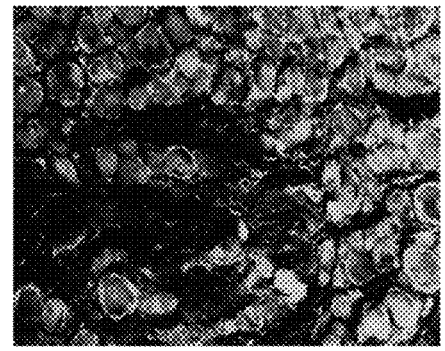
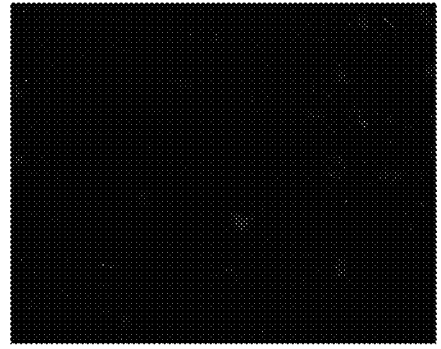
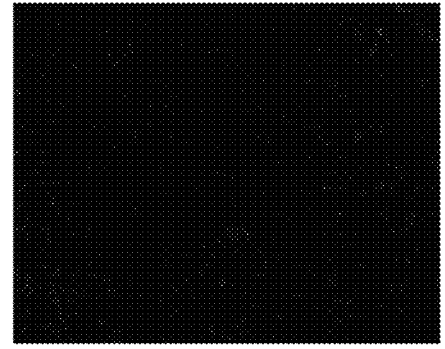

[Fig. 15]
IHC: 1 day after transforaminal epidural injection
Dorsal root ganglion (DRG), X200
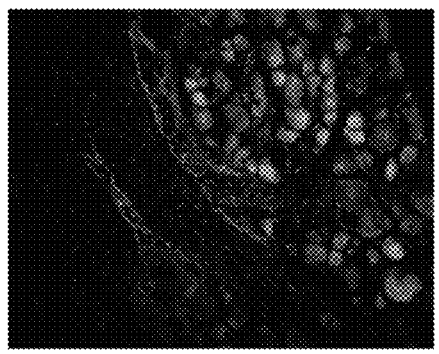
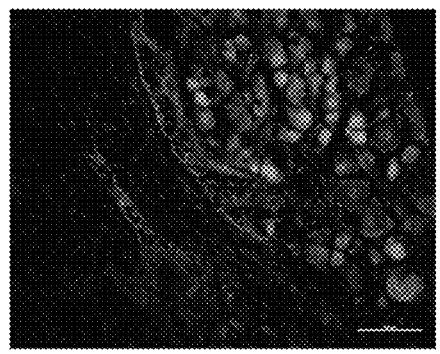
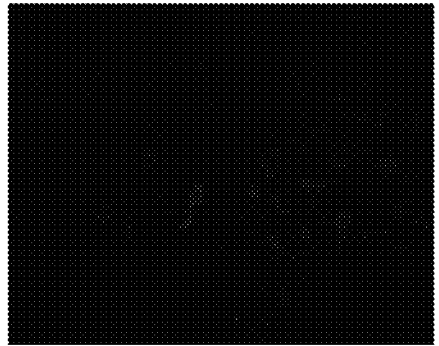
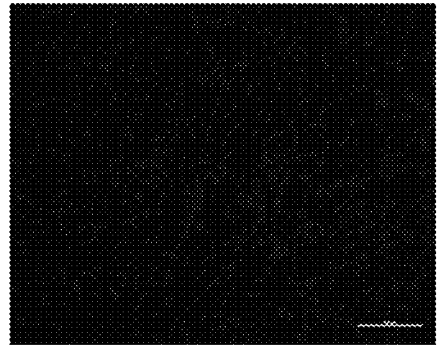

【Fig. 16】
Transforaminal epidural injection in dog
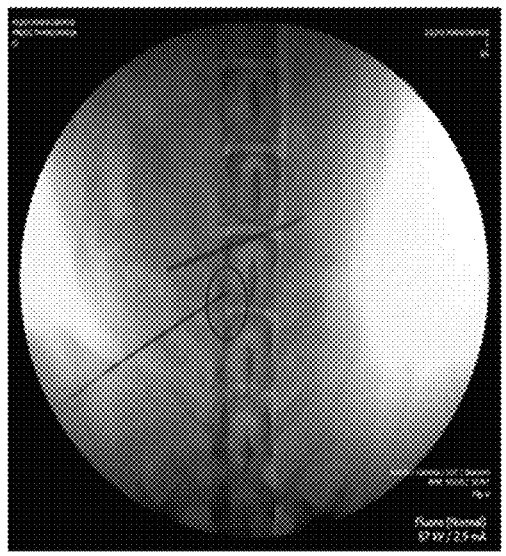 
vertical view      lateral view
【Fig. 17】
Transforaminal epidural injection in micro-pig
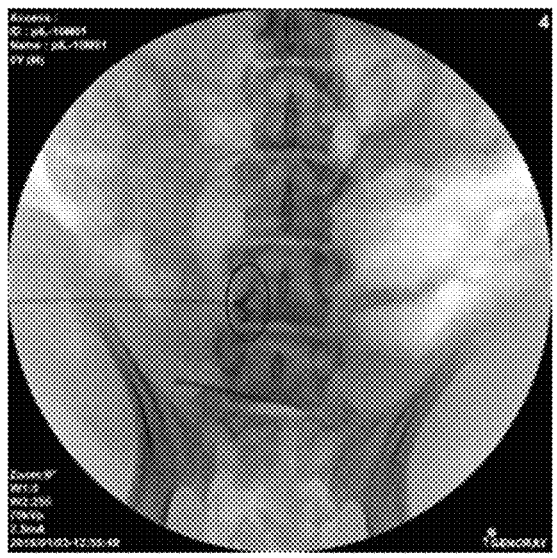 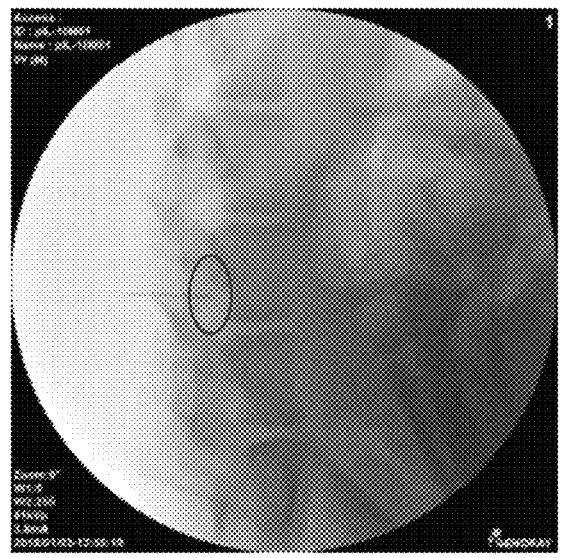
vertical view      lateral view

SEQUENCE LISTING

<160> NUMBER OF SEQ ID NOS: 33

<210> SEQ ID NO 1
<211> LENGTH: 585
<212> TYPE: PRT
<213> ORGANISM: Homo sapiens

<400> SEQUENCE: 1

Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

```
Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
    130                 135                 140

Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
            180                 185                 190

Ala Asp Trp Leu Thr Ser Thr Ala Asn Thr Asn Met Phe Thr Tyr Glu
        195                 200                 205

Ile Ala Pro Val Phe Val Leu Leu Glu Tyr Val Thr Leu Lys Lys Met
    210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
            260                 265                 270

Leu Ile Ala Phe Thr Ser Glu His Ser His Phe Ser Leu Lys Lys Gly
        275                 280                 285

Ala Ala Ala Leu Gly Ile Gly Thr Asp Ser Val Ile Leu Ile Lys Cys
    290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
            340                 345                 350

Ile Cys Lys Lys Tyr Lys Ile Trp Met His Val Asp Ala Ala Trp Gly
        355                 360                 365

Gly Gly Leu Leu Met Ser Arg Lys His Lys Trp Lys Leu Ser Gly Val
    370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
            420                 425                 430

Tyr Asp Leu Ser Tyr Asp Thr Gly Asp Lys Ala Leu Gln Cys Gly Arg
        435                 440                 445

His Val Asp Val Phe Lys Leu Trp Leu Met Trp Arg Ala Lys Gly Thr
    450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
            500                 505                 510
```

```
Leu Arg Thr Leu Glu Asp Asn Glu Glu Arg Met Ser Arg Leu Ser Lys
            515                 520                 525

Val Ala Pro Val Ile Lys Ala Arg Met Met Glu Tyr Gly Thr Thr Met
        530                 535                 540

Val Ser Tyr Gln Pro Leu Gly Asp Lys Val Asn Phe Phe Arg Met Val
545                 550                 555                 560

Ile Ser Asn Pro Ala Ala Thr His Gln Asp Ile Asp Phe Leu Ile Glu
                565                 570                 575

Glu Ile Glu Arg Leu Gly Gln Asp Leu
            580                 585

<210> SEQ ID NO 2
<211> LENGTH: 2824
<212> TYPE: DNA
<213> ORGANISM: Homo sapiens

<400> SEQUENCE: 2
gcggccgccc gcacttcccg cctctggctc gcccgaggac gcgctggcac gcctcccacc      60
ccctcactct gactccagct ggcgtgcatg gtctgcctcg catcctcacg actcagctcc     120
ctccctctct cgtgtttttt tcctccgccg cccctcatt catccccact gggctccctt      180
tccctcaaat gctctggggc tctccgcgct ttcctgagtc cgggctccga ggacccttag     240
gtagtcccgg tctctttaa agctccccgg cttccaaagg gttgccacgt ccctaaaccc      300
tgtctccagc tcgcatacac acacgcacag acacgcacgt tttctgttcc tgcgtgacac     360
ccgccctcgc cgctcggccc cgccggtccc cgcgcggtgc cctcctcccg ccacacgggc     420
acgcacgcgc gcgcagggcc aagcccgagg cagctcgccc gcagctcgca ctcgcaggcg     480
acctgctcca gtctccaaag ccgatggcat tccgggctc tggcttttgg tctttcgggt      540
cggaagatgg ctctggggat ccgagaatc ccggcacagc gcgagcctgg tgccaagtgg      600
ctcagaagtt cacgggcggc atcggaaaca aactgtgcgc cctgctctac ggagacgccg     660
agaagccggc ggagagcggc gggagccaac ccccgcgggc cgccgcccgg aaggccgcct     720
gcgcctgcga ccagaagccc tgcagctgct ccaaagtgga tgtcaactac cgtttctcc      780 atgcaacaga cctgctgccg gcgtgtgatg agaaaggcc cactttggcg tttctgcaag     840
atgttatgaa cattttactt cagtatgtgg tgaaaagttt cgatagatca accaaagtga     900
ttgattttca ttatcctaat gagcttctcc aagaatataa ttgggaattg gcagaccaac     960
cacaaaattt ggaggaaatt ttgatgcatt gccaaacaac tctaaaatat gcaattaaaa    1020
cagggcatcc tagatacttc aatcaacttt ctactggttt ggatatggtt ggattagcag    1080
cagactggct gacatcaaca gcaaatacta acatgttcac ctatgaaatt gctccagtat    1140
ttgtgctttt ggaatatgtc acactaaaga aaatgagaga atcattggc tggccagggg     1200 gctctggcga tgggatattt tctcccggtg gcgccatatc taacatgtat gccatgatga    1260
tcgcacgctt taagatgttc ccagaagtca aggagaaagg aatggctgct cttcccaggc    1320
tcattgcctt cacgtctgaa catagtcatt tttctctcaa gaagggagct gcagccttag    1380
ggattggaac agacagcgtg attctgatta aatgtgatga gagagggaaa atgattccat    1440
ctgatcttga aagaaggatt cttgaagcca acagaaagg gtttgttcct ttcctcgtga    1500
gtgccacagc tggaaccacc gtgtacggag catttgaccc cctcttagct gtcgctgaca    1560
tttgcaaaaa gtataagatc tggatgcatg tggatgcagc ttggggtggg ggattactga    1620
tgtcccgaaa acacaagtgg aaactgagtg gcgtggagag ggccaactct gtgacgtgga    1680
```

| | |
|---|---|
| atccacacaa gatgatggga gtcccttttgc agtgctctgc tctcctggtt agagaagagg | 1740 |
| gattgatgca gaattgcaac caaatgcatg cctcctacct ctttcagcaa gataaacatt | 1800 |
| atgacctgtc ctatgacact ggagacaagg ccttacagtg cggacgccac gttgatgttt | 1860 |
| ttaaactatg gctgatgtgg agggcaaagg ggactaccgg gtttgaagcg catgttgata | 1920 |
| aatgtttgga gttggcagag tatttataca acatcataaa aaaccgagaa ggatatgaga | 1980 |
| tggtgtttga tgggaagcct cagcacacaa atgtctgctt ctggtacatt cctccaagct | 2040 |
| tgcgtactct ggaagacaat aagagagaa tgagtcgcct ctcgaaggtg gctccagtga | 2100 |
| ttaaagccag aatgatggag tatgaaacca caatggtcag ctaccaaccc ttgggagaca | 2160 |
| aggtcaattt cttccgcatg gtcatctcaa acccagcggc aactcaccaa gacattgact | 2220 |
| tcctgattga gaaatagaa cgccttggac aagatttata ataaccttgc tcaccaagct | 2280 |
| gttccacttc tctagagaac atgccctcag ctaagccccc tactgagaaa cttcctttga | 2340 |
| gaattgtgcg acttcacaaa atgcaaggtg aacaccactt tgtctctgag aacagacgtt | 2400 |
| accaattatg gagtgtcacc agctgccaaa atcgtaggtg ttggctctgc tggtcactgg | 2460 |
| agtagttgct actcttcaga atatggacaa agaaggcaca ggtgtaaata tagtagcagg | 2520 |
| atgaggaacc tcaaactggg tatcattttg cacgtgctct tctgttctca aatgctaaat | 2580 |
| gcaaacactg tgtatttatt agttaggtgt gccaaactac cgttcccaaa ttggtgtttc | 2640 |
| tgaatgacat caacattccc ccaacattac tccattacta aagacagaaa aaaataaaaa | 2700 |
| cataaaatat acaaacatgt ggcaacctgt tcttcctacc aaatataaac ttgtgtatga | 2760 |
| tccaagtatt ttatctgtgt tgtctctcta aacccaaata aatgtgtaaa tgtggacaca | 2820 |
| tctc | 2824 |

<210> SEQ ID NO 3
<211> LENGTH: 1758
<212> TYPE: DNA
<213> ORGANISM: Artificial Sequence
<220> FEATURE:
<223> OTHER INFORMATION: Optimized human GAD65

<400> SEQUENCE: 3

| | |
|---|---|
| atggcatctc cgggctccgg cttttggtcc ttcgggtcgg aagatggctc aggggattcc | 60 |
| gagaatcccg gcacagcgcg ggcctggtgt caagtggctc agaagttcac gggcggcatc | 120 |
| ggaaacaaac tgtgtgccct gctctacggc gacgccgaga agcccgcaga gagcggcggg | 180 |
| agccaacccc gcgggccgc cgcccggaag ccgccctgcg cctgtgacca gaagccctgc | 240 |
| tcatgcagca aggtagatgt caactacgcg tttctccatg ccacagatct gctgccggct | 300 |
| tgcgacggtg aaaggcccac tttggccttt ctgcaggatg ttatgaacat tctgctgcag | 360 |
| tacgtggtga aaagtttcga ccggtcaacc aaagtgatcg actttcacta tcctaatgaa | 420 |
| cttctccagg agtacaattg ggagctggcc gaccagccac agaacctgga ggaaatcttg | 480 |
| atgcattgcc aaactactct aaaatatgca attaaaacag gccatcctag atacttcaac | 540 |
| cagcttttcta ccggtttgga tatggtgggg ctggcagccg actggctgac atccaccgca | 600 |
| aataccaaca tgttcaccta tgagatcgct cctgtcttcg tgcttttgga atacgtcacc | 660 |
| ctaaagaaga tgcgtgaaat cattggctgg ccaggaggct ctggtgatgg tatatttttct | 720 |
| cccggcggcg cgatctctaa catgtatgcc atgatgatcg cacgctttaa gatgttccca | 780 |
| gaagtcaagg agaaaggaat ggctgctctt cccaggctca ttgccttcac gagtgaacac | 840 |
| agtcactttt ccctcaagaa gggggctgcc gccttaggga tcggaacaga cagcgtgatt | 900 |

```
ctgataaagt gcgacgagag agggaaaatg attccatctg atcttgagag aaggattctt    960
gaagccaaac agaaagggtt tgtccctttc ctcgtgagtg ccacagctgg aaccaccgtg   1020
tacggcgcat ttgaccccct cttagctgtc gcggatatat gtaagaagta aagatctgg   1080
atgcacgtgg atgctgcttg gggtggggga ttactgatgt ccaggaaaca caagtggaaa   1140
ctgtctggcg tggagcgcgc caacagcgtg acgtggaatc cacacaaaat gatgggagtc   1200
cctttgcagt gctctgctct cctggttcga aagagggac tgatgcagaa ttgcaaccaa    1260
atgcatgcct cctacctctt tcagcaggat aaacattatg acctgtctta cgacactggt   1320
gacaaggccc tgcagtgtgg gcgccacgtt gatgtattca agctatggct gatgtggagg   1380
gcaaaggga ctaccggttt tgaagcccat gttgacaaat gtctggagtt ggcagagtat    1440
ttatacaata tcataaaaaa ccgagaagga tatgagatgg tgtttgatgg caagcctcag   1500
cacacaaatg tctgcttctg gtacatccct cccagcctac gtactctgga ggacaacgaa   1560
gagagaatga gtcgcctctc gaaggtggct ccagtgatta agccagaat gatggagtat    1620
ggaaccacaa tggtcagcta ccaacccttg ggggacaagg taaatttctt ccgcatggtc   1680
atctcaaacc cagcggcaac tcaccaagac attgatttcc tgattgaaga gatcgagcgg   1740
ctcggccagg atctgtga                                                  1758

<210> SEQ ID NO 4
<211> LENGTH: 594
<212> TYPE: PRT
<213> ORGANISM: Homo sapiens

<400> SEQUENCE: 4

Met Ala Ser Ser Thr Pro Ser Ser Ala Thr Ser Ser Asn Ala Gly
1               5                   10                  15

Ala Asp Pro Asn Thr Thr Asn Leu Arg Pro Thr Thr Tyr Asp Thr Trp
                20                  25                  30

Cys Gly Val Ala His Gly Cys Thr Arg Lys Leu Gly Leu Lys Ile Cys
            35                  40                  45

Gly Phe Leu Gln Arg Thr Asn Ser Leu Glu Glu Lys Ser Arg Leu Val
        50                  55                  60

Ser Ala Phe Lys Glu Arg Gln Ser Ser Lys Asn Leu Leu Ser Cys Glu
65                  70                  75                  80

Asn Ser Asp Arg Asp Ala Arg Phe Arg Arg Thr Glu Thr Asp Phe Ser
                85                  90                  95

Asn Leu Phe Ala Arg Asp Leu Leu Pro Ala Lys Asn Gly Glu Glu Gln
            100                 105                 110

Thr Val Gln Phe Leu Leu Glu Val Val Asp Ile Leu Leu Asn Tyr Val
        115                 120                 125

Arg Lys Thr Phe Asp Arg Ser Thr Lys Val Leu Asp Phe His His Pro
    130                 135                 140

His Gln Leu Leu Glu Gly Met Glu Gly Phe Asn Leu Glu Leu Ser Asp
145                 150                 155                 160

His Pro Glu Ser Leu Glu Gln Ile Leu Val Asp Cys Arg Asp Thr Leu
                165                 170                 175

Lys Tyr Gly Val Arg Thr Gly His Pro Arg Phe Phe Asn Gln Leu Ser
            180                 185                 190

Thr Gly Leu Asp Ile Ile Gly Leu Ala Gly Glu Trp Leu Thr Ser Thr
        195                 200                 205

Ala Asn Thr Asn Met Phe Thr Tyr Glu Ile Ala Pro Val Phe Val Leu
```

```
            210                 215                 220
Met Glu Gln Ile Thr Leu Lys Lys Met Arg Glu Ile Val Gly Trp Ser
225                 230                 235                 240

Ser Lys Asp Gly Asp Gly Ile Phe Ser Pro Gly Ala Ile Ser Asn
                245                 250                 255

Met Tyr Ser Ile Met Ala Ala Arg Tyr Lys Tyr Phe Pro Glu Val Lys
                260                 265                 270

Thr Lys Gly Met Ala Ala Val Pro Lys Leu Val Leu Phe Thr Ser Glu
                275                 280                 285

Gln Ser His Tyr Ser Ile Lys Lys Ala Gly Ala Ala Leu Gly Phe Gly
                290                 295                 300

Thr Asp Asn Val Ile Leu Ile Lys Cys Asn Glu Arg Gly Lys Ile Ile
305                 310                 315                 320

Pro Ala Asp Phe Glu Ala Lys Ile Leu Glu Ala Lys Gln Lys Gly Tyr
                325                 330                 335

Val Pro Phe Tyr Val Asn Ala Thr Ala Gly Thr Thr Val Tyr Gly Ala
                340                 345                 350

Phe Asp Pro Ile Gln Glu Ile Ala Asp Ile Cys Glu Lys Tyr Asn Leu
                355                 360                 365

Trp Leu His Val Asp Ala Ala Trp Gly Gly Gly Leu Leu Met Ser Arg
370                 375                 380

Lys His Arg His Lys Leu Asn Gly Ile Glu Arg Ala Asn Ser Val Thr
385                 390                 395                 400

Trp Asn Pro His Lys Met Met Gly Val Leu Leu Gln Cys Ser Ala Ile
                405                 410                 415

Leu Val Lys Glu Lys Gly Ile Leu Gln Gly Cys Asn Gln Met Cys Ala
                420                 425                 430

Gly Tyr Leu Phe Gln Pro Asp Lys Gln Tyr Asp Val Ser Tyr Asp Thr
                435                 440                 445

Gly Asp Lys Ala Ile Gln Cys Gly Arg His Val Asp Ile Phe Lys Phe
                450                 455                 460

Trp Leu Met Trp Lys Ala Lys Gly Thr Val Gly Phe Glu Asn Gln Ile
465                 470                 475                 480

Asn Lys Cys Leu Glu Leu Ala Glu Tyr Leu Tyr Ala Lys Ile Lys Asn
                485                 490                 495

Arg Glu Glu Phe Glu Met Val Phe Asn Gly Glu Pro Glu His Thr Asn
                500                 505                 510

Val Cys Phe Trp Tyr Ile Pro Gln Ser Leu Arg Gly Val Pro Asp Ser
                515                 520                 525

Pro Gln Arg Arg Glu Lys Leu His Lys Val Ala Pro Lys Ile Lys Ala
                530                 535                 540

Leu Met Met Glu Ser Gly Thr Thr Met Val Gly Tyr Gln Pro Gln Gly
545                 550                 555                 560

Asp Lys Ala Asn Phe Phe Arg Met Val Ile Ser Asn Pro Ala Ala Thr
                565                 570                 575

Gln Ser Asp Ile Asp Phe Leu Ile Glu Ile Glu Arg Leu Gly Gln
                580                 585                 590

Asp Leu

<210> SEQ ID NO 5
<211> LENGTH: 1784
<212> TYPE: DNA
<213> ORGANISM: Homo sapiens
```

<400> SEQUENCE: 5

```
atggcgtctc gacccatct tcgtccgcaa cctcctcgaa cgcgggagcg gaccccaata    60
ccactaacct gcgccccaca acgtacgata cctggtgcgg cgtggcccat ggatgcacca   120
gaaaactggg gctcaagatc tgcggcttct tgcaaaggac caacagcctg aagagaaga   180
gtcgccttgt gagtgccttc aaggagaggc aatcctccaa gaacctgctt tcctgtgaaa   240
acagcgaccg ggatgcccgc ttccggcgca cagagactga cttctctaat ctgtttgcta   300
gagatctgct tccggctaag aacggtgagg agcaaaccgt gcaattcctc tggaagtgg   360
tggacatact cctcaactat gtccgcaaga catttgatcg ctccaccaag gtgctggact   420
ttcatcaccc acaccagttg ctggaaggca tggagggctt caacttggag ctctctgacc   480
accccgagtc cctggagcag atcctggttg actgcagaga caccttgaag tatggggttc   540
gcacaggtca tcctcgattt ttcaaccagc tctccactgg attggatatt attggcctag   600
ctggagaatg gctgacatca acggccaata ccaacatgtt tacatatgaa attgcaccag   660
tgtttgtcct catggaacaa ataacactta agaagatgag agagatagtt ggatggtcaa   720
gtaaagatgg tgatgggata ttttctcctg ggggcgccat atccaacatg tacagcatca   780
tggctgctcg ctacaagtac ttcccggaag ttaagacaaa gggcatggcg gctgtgccta   840
aactggtcct cttcacctca gaacagagtc actattccat aaagaaagct ggggctgcac   900
ttggctttgg aactgacaat gtgatttga taaagtgcaa tgaaagggg aaataattc   960
cagctgattt tgaggcaaaa attcttgaag ccaaacagaa gggatatgtt cccttttatg  1020
tcaatgcaac tgctggcacg actgtttatg agcttttga tccgatacaa gagattgcag  1080
atatatgtga gaaatataac ctttggttgc atgtcgatgc tgcctgggga ggtgggctgc  1140
tcatgtccag gaagcaccgc cataaactca acggcataga aagggccaac tcagtcacct  1200
ggaaccctca agatgatg ggcgtgctgt tgcagtgctc tgccattctc gtcaaggaaa  1260
agggtatact ccaaggatgc aaccagatgt gtgcaggata cctcttccag ccagacaagc  1320
agtatgatgt ctcctacgac accggggaca aggcaattca gtgtggccgc cacgtggata  1380
tcttcaagtt ctggctgatg tggaaagcaa agggcacagt gggatttgaa accagatca  1440
acaaatgcct ggaactggct gaatacctct atgccaagat taaaaacaga gaagaatttg  1500
agatggtttt caatggcgag cctgagcaca caaacgtctg ttttttggtat attccacaaa  1560
gcctcagggg tgtgccagac agccctcaac gacgggaaaa gctacacaag gtggctccaa  1620
aaatcaaagc cctgatgatg gagtcaggta cgaccatggt tggctaccag ccccaagggg  1680
acaaggccaa cttcttccgg atggtcatct ccaacccagc cgctacccag tctgacattg  1740
acttcctcat tgaggagata gaaagactgg gccaggatct gtaa              1784
```

<210> SEQ ID NO 6
<211> LENGTH: 178
<212> TYPE: PRT
<213> ORGANISM: Rattus norvegicus

<400> SEQUENCE: 6

```
Met Pro Gly Ser Ala Leu Leu Cys Cys Leu Leu Leu Leu Ala Gly Val
1               5                   10                  15

Lys Thr Ser Lys Gly His Ser Ile Arg Gly Asp Asn Asn Cys Thr His
                20                  25                  30

Phe Pro Val Ser Gln Thr His Met Leu Arg Glu Leu Arg Ala Ala Phe
            35                  40                  45
```

```
Ser Gln Val Lys Thr Phe Phe Gln Lys Lys Asp Gln Leu Asp Asn Ile
    50              55                  60
Leu Leu Thr Asp Ser Leu Leu Gln Asp Phe Lys Gly Tyr Leu Gly Cys
65              70                  75                  80
Gln Ala Leu Ser Glu Met Ile Lys Phe Tyr Leu Val Glu Val Met Pro
                85                  90                  95
Gln Ala Glu Asn His Gly Pro Glu Ile Lys Glu His Leu Asn Ser Leu
                100                 105                 110
Gly Glu Lys Leu Lys Thr Leu Trp Ile Gln Leu Arg Arg Cys His Arg
                115                 120                 125
Phe Leu Pro Cys Glu Asn Lys Ser Lys Ala Val Glu Gln Val Lys Asn
130                 135                 140
Asp Phe Asn Lys Leu Gln Asp Lys Gly Val Tyr Lys Ala Met Asn Glu
145                 150                 155                 160
Phe Asp Ile Phe Ile Asn Cys Ile Glu Ala Tyr Val Thr Leu Lys Met
                165                 170                 175
Lys Asn
```

<210> SEQ ID NO 7
<211> LENGTH: 682
<212> TYPE: DNA
<213> ORGANISM: Rattus norvegicus

<400> SEQUENCE: 7

```
catgcctggc tcagcactgc tatgttgcct gctcttactg gctggagtga agaccagcaa    60
aggccattcc atccggggtg acaataactg cacccacttc ccagtcagcc agacccacat   120
gctccgagag ctgagggctg ccttcagtca agtgaagact ttctttcaaa agaaggacca   180
gctggacaac atactgctga cagattcctt actgcaggac tttaagggtt acttgggttg   240
ccaagccttg tcagaaatga tcaagtttta cctggtagaa gtgatgcccc aggcagagaa   300
ccatggccca gaaatcaagg agcatttgaa ttccctggga gagaagctga gaccctctg   360
gatacagctg cgacgctgtc atcgatttct cccctgtgag aataaaagca aggcagtgga   420
gcaggtgaag aatgatttta ataagctcca agacaaaggt gtctacaagg ccatgaatga   480
gtttgacatc ttcatcaact gcatagaagc ctacgtgaca ctcaaaatga aaattgaac   540
cacccggcat ctactggact gcaggacata aatagagctt ctaaatctga tccagagatc   600
ttagctaacg ggagcaactc cttggaaaac ctcgtttgta cctctctcca aaatatttat   660
tacctctgat acctcagttc cc                                             682
```

<210> SEQ ID NO 8
<211> LENGTH: 537
<212> TYPE: DNA
<213> ORGANISM: Artificial Sequence
<220> FEATURE:
<223> OTHER INFORMATION: Optimized rat IL-10

<400> SEQUENCE: 8

```
atgcctggct cagccctgct atgttgcctt ctcctgctgg cgggagtcaa gacaagcaag    60
ggccattcca tccggggaga taataactgc acccacttcc cagtctctca aacccacatg   120
ttgcgagagc tgagggctgc cttcagtcag gtgaagacgt tcttccagaa gaaggaccag   180
ctggacaaca ttctgctgac tgacagcctg ctgcaggatt caagggtta tttggggtgt   240
caagccctgt ctgaaatgat caagttttac ctggtagaag tgatgcccca ggcagagaat   300
catggccccg agatcaagga gcacctcaac tccctggggg agaagctgaa gaccctgtgg   360
```

```
attcagctga ggcgctgcca cagatttctc ccctgtgaaa acaagagcaa ggcagtggag      420
caggtgaaga acgattttaa taagctccag gacaagggcg tctacaaggc catgaacgag      480
ttcgacatct ttatcaactg catagaagct tacgttacac tcaagatgaa gaattga        537
```

<210> SEQ ID NO 9
<211> LENGTH: 178
<212> TYPE: PRT
<213> ORGANISM: Homo sapiens

<400> SEQUENCE: 9

```
Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

<210> SEQ ID NO 10
<211> LENGTH: 1600
<212> TYPE: DNA
<213> ORGANISM: Homo sapiens

<400> SEQUENCE: 10

```
aaaccacaag acagacttgc aaaagaaggc atgcacagct cagcactgct ctgttgcctg       60
gtcctcctga ctggggtgag ggccagccca ggccagggca cccagtctga aacagctgc      120 acccacttcc caggcaacct gcctaacatg cttcgagatc tccgagatgc cttcagcaga      180
gtgaagactt tctttcaaat gaaggatcag ctggacaact tgttgttaaa ggagtccttg      240
ctggaggact ttaagggtta cctgggttgc caagccttgt ctgagatgat ccagttttac      300
ctggaggagg tgatgcccca agctgagaac caagacccag acatcaaggc gcatgtgaac      360
tccctggggg agaacctgaa gaccctcagg ctgaggctac ggcgctgtca tcgatttctt      420
ccctgtgaaa acaagagcaa ggccgtggag caggtgaaga atgcctttaa taagctccaa      480
gagaaaggca tctacaaagc catgagtgag tttgacatct tcatcaacta catagaagcc      540
tacatgacaa tgaagatacg aaactgagac atcagggtgg cgactctata gactctagga      600
cataaattag aggtctccaa aatcggatct ggggctctgg atagctgac ccagccccctt      660
```

| | |
|---|---|
| gagaaacctt attgtacctc tcttatagaa tatttattac ctctgatacc tcaaccccca | 720 |
| tttctattta tttactgagc ttctctgtga acgatttaga aagaagccca atattataat | 780 |
| ttttttcaat atttattatt ttcacctgtt tttaagctgt ttccataggg tgacacacta | 840 |
| tggtatttga gtgttttaag ataaattata agttacataa gggaggaaaa aaaatgttct | 900 |
| ttggggagcc aacagaagct tccattccaa gcctgaccac gctttctagc tgttgagctg | 960 |
| ttttccctga cctccctcta atttatcttg tctctgggct tggggcttcc taactgctac | 1020 |
| aaatactctt aggaagagaa accagggagc cctttgatg attaattcac cttccagtgt | 1080 |
| ctcggaggga ttcccctaac ctcattcccc aaccacttca ttcttgaaag ctgtggccag | 1140 |
| cttgttattt ataacaacct aaatttggtt ctaggccggg cgcggtggct cacgcctgta | 1200 |
| atcccagcac tttgggaggc tgaggcgggt ggatcacttg aggtcaggag ttcctaacca | 1260 |
| gcctggtcaa catggtgaaa ccccgtctct actaaaaata caaaaattag ccgggcatgg | 1320 |
| tggcgcgcac ctgtaatccc agctacttgg gaggctgagg caagagaatt gcttgaaccc | 1380 |
| aggagatgga agttgcagtg agctgatatc atgcccctgt actccagcct gggtgacaga | 1440 |
| gcaagactct gtctcaaaaa ataaaaataa aataaatttt ggttctaata gaactcagtt | 1500 |
| ttaactagaa tttattcaat tcctctggga atgttacatt gtttgtctgt cttcatagca | 1560 |
| gattttaatt ttgaataaat aaatgtatct tattcacatc | 1600 |

<210> SEQ ID NO 11
<211> LENGTH: 147
<212> TYPE: PRT
<213> ORGANISM: Rattus norvegicus

<400> SEQUENCE: 11

Met Gly Leu Ser Pro His Leu Ala Val Thr Leu Phe Cys Phe Leu Ile
1               5                   10                  15

Cys Thr Gly Asn Gly Ile His Gly Cys Asn Asp Ser Pro Leu Arg Glu
            20                  25                  30

Ile Ile Asn Thr Leu Asn Gln Val Thr Glu Lys Gly Thr Pro Cys Thr
        35                  40                  45

Glu Met Phe Val Pro Asp Val Leu Thr Ala Thr Arg Asn Thr Thr Glu
    50                  55                  60

Asn Glu Leu Ile Cys Arg Ala Ser Arg Val Leu Arg Lys Phe Tyr Phe
65                  70                  75                  80

Pro Arg Asp Val Pro Pro Cys Leu Lys Asn Lys Ser Gly Val Leu Gly
                85                  90                  95

Glu Leu Arg Lys Leu Cys Arg Gly Val Ser Gly Leu Asn Ser Leu Arg
            100                 105                 110

Ser Cys Thr Val Asn Glu Ser Thr Leu Thr Thr Leu Lys Asp Phe Leu
        115                 120                 125

Glu Ser Leu Lys Ser Ile Leu Arg Gly Lys Tyr Leu Gln Ser Cys Thr
    130                 135                 140

Ser Met Ser
145

<210> SEQ ID NO 12
<211> LENGTH: 475
<212> TYPE: DNA
<213> ORGANISM: Rattus norvegicus

<400> SEQUENCE: 12

```
tctcacgtca ctgactgtag agagctattg atgggtctca gccccacct tgctgtcacc      60 ctgttctgct ttctcatatg taccgggaac ggtatccacg gatgtaacga cagccctctg    120
agagagatca tcaacacttt gaaccaggtc acagaaaaag ggactccatg caccgagatg    180
tttgtaccag acgtccttac ggcaacaagg aacaccacgg agaacgagct catctgcagg    240
gcttccaggg tgcttcgcaa attttacttc ccacgtgatg tacctccgtg cttgaagaac    300
aagtctgggg ttctcggtga actgaggaaa ctctgtagag gtgtcagcgg tctgaactca    360
ctgagaagct gcaccgtgaa tgagtccacg ctcacaacac tgaaagactt cctggaaagc    420
ctaaaaagca tcctacgagg gaaatacttg cagtcctgca cttccatgtc ctaac         475
```

<210> SEQ ID NO 13
<211> LENGTH: 444
<212> TYPE: DNA
<213> ORGANISM: Artificial Sequence
<220> FEATURE:
<223> OTHER INFORMATION: Optimized rat IL-4

<400> SEQUENCE: 13

```
atgggtttaa gccccacct tgccgtcaca ctgttctgtt ttctcatctg taccgggaac      60
ggaattcatg gctgtaacga cagccctctg agagagatta tcaacacctt gaatcaggtt    120
accgaaaaag gcactccatg caccgagatg tttgtaccag atgtgcttac ggcaacgagg    180
aacaccactg agaatgagct gatctgtcgg gcttctcgag tgctgcgcaa attctacttc    240
cctcgtgatg tgcccccgtg cttgaagaac aagtcaggcg tgctcggaga actgaggaag    300
ctctgcagag gcgtctcagg gctgaattct gtgcgcagct gcaccgtgaa tgaatccaca    360
ctcacaaccc tgaaagactt cctggagagc ctgaagagca tcctacgggg gaagtatctc    420
cagtcctgca cttccatgag ttga                                            444
```

<210> SEQ ID NO 14
<211> LENGTH: 153
<212> TYPE: PRT
<213> ORGANISM: Homo sapiens

<400> SEQUENCE: 14

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
                20                  25                  30

Glu Ile Ile Lys Thr Leu Asn Ser Leu Thr Glu Gln Lys Thr Leu Cys
            35                  40                  45

Thr Glu Leu Thr Val Thr Asp Ile Phe Ala Ala Ser Lys Asn Thr Thr
        50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
    130                 135                 140

Arg Glu Lys Tyr Ser Lys Cys Ser Ser
145                 150

```
<210> SEQ ID NO 15
<211> LENGTH: 642
<212> TYPE: DNA
<213> ORGANISM: Homo sapiens

<400> SEQUENCE: 15
tgcatcgtta gcttctcctg ataaactaat tgcctcacat tgtcactgca aatcgacacc      60
tattaatggg tctcacctcc caactgcttc cccctctgtt cttcctgcta gcatgtgccg     120
gcaactttgt ccacggacac aagtgcgata tcaccttaca ggagatcatc aaaactttga     180
acagcctcac agagcagaag actctgtgca ccgagttgac cgtaacagac atctttgctg     240
cctccaagaa cacaactgag aaggaaacct tctgcagggc tgcgactgtg ctccggcagt     300
tctacagcca ccatgagaag gacactcgct gcctgggtgc gactgcacag cagttccaca     360
ggcacaagca gctgatccga ttcctgaaac ggctcgacag gaacctctgg ggcctggcgg     420
gcttgaattc ctgtcctgtg aaggaagcca accagagtac gttggaaaac ttcttggaaa     480
ggctaaagac gatcatgaga gagaaatatt caaagtgttc gagctgaata tttaattta     540 tgagttttg atagctttat tttttaagta tttatatatt tataactcat cataaaataa     600
agtatatata gaatctaaaa aaaaaaaaaa aaaaaaaaaa aa                       642

<210> SEQ ID NO 16
<211> LENGTH: 28
<212> TYPE: DNA
<213> ORGANISM: Artificial Sequence
<220> FEATURE:
<223> OTHER INFORMATION: Forward primer for amplifying CMV promoter

<400> SEQUENCE: 16
ttcggccgtc gaggagcttg gcccattg                                        28

<210> SEQ ID NO 17
<211> LENGTH: 36
<212> TYPE: DNA
<213> ORGANISM: Artificial Sequence
<220> FEATURE:
<223> OTHER INFORMATION: Reverse primer for amplifying CMV promoter

<400> SEQUENCE: 17
gacgtcgacc tagctagcga attcggggcc gcggag                               36

<210> SEQ ID NO 18
<211> LENGTH: 34
<212> TYPE: DNA
<213> ORGANISM: Artificial Sequence
<220> FEATURE:
<223> OTHER INFORMATION: Forward primer for amplifying SV40pA

<400> SEQUENCE: 18
ccatcgatca gacatgataa gatacattga tgag                                 34

<210> SEQ ID NO 19
<211> LENGTH: 43
<212> TYPE: DNA
<213> ORGANISM: Artificial Sequence
<220> FEATURE:
<223> OTHER INFORMATION: Reverse primer for amplifying SV40pA

<400> SEQUENCE: 19
gacgtcgacg cggccgctac cacatttgta gaggttttac ttg                       43
```

<210> SEQ ID NO 20
<211> LENGTH: 28
<212> TYPE: DNA
<213> ORGANISM: Artificial Sequence
<220> FEATURE:
<223> OTHER INFORMATION: Forward primer for amplifying Kanamycin
      resistant gene

<400> SEQUENCE: 20
aggcgccatg agccatattc aacgggaa                                      28

<210> SEQ ID NO 21
<211> LENGTH: 29
<212> TYPE: DNA
<213> ORGANISM: Artificial Sequence
<220> FEATURE:
<223> OTHER INFORMATION: Reverse primer for amplifying Kanamycin
      resistant gene

<400> SEQUENCE: 21
ttcatgatta gaaaaactca tcgagcatc                                     29

<210> SEQ ID NO 22
<211> LENGTH: 28
<212> TYPE: DNA
<213> ORGANISM: Artificial Sequence
<220> FEATURE:
<223> OTHER INFORMATION: Forward primer for amplifying LITR and CMV

<400> SEQUENCE: 22
atggcgcgcc cctggccttt tgctggcc                                      28

<210> SEQ ID NO 23
<211> LENGTH: 28
<212> TYPE: DNA
<213> ORGANISM: Artificial Sequence
<220> FEATURE:
<223> OTHER INFORMATION: Reverse primer for amplifying SV40pA and RITR

<400> SEQUENCE: 23
atggatccgc tagtaaatac cgcatcag                                      28

<210> SEQ ID NO 24
<211> LENGTH: 20
<212> TYPE: DNA
<213> ORGANISM: Artificial Sequence
<220> FEATURE:
<223> OTHER INFORMATION: Forward primer for amplifying rIL-10

<400> SEQUENCE: 24
ccgctagcgc caccatgcct                                               20

<210> SEQ ID NO 25
<211> LENGTH: 39
<212> TYPE: DNA
<213> ORGANISM: Artificial Sequence
<220> FEATURE:
<223> OTHER INFORMATION: Reverse primer for amplifying rIL-10

<400> SEQUENCE: 25
gacgtcgacg ccatcgatgg cttaattaat caattcttc                          39

<210> SEQ ID NO 26
<211> LENGTH: 24
<212> TYPE: DNA
<213> ORGANISM: Artificial Sequence

```
<220> FEATURE:
<223> OTHER INFORMATION: nucleotide seqeunce of Flag

<400> SEQUENCE: 26
gattacaagg atgacgacga taag                                           24

<210> SEQ ID NO 27
<211> LENGTH: 42
<212> TYPE: DNA
<213> ORGANISM: Artificial Sequence
<220> FEATURE:
<223> OTHER INFORMATION: nucleotide seqeunce of Scramble stuffer

<400> SEQUENCE: 27
gtcgacggta tcgataagct tgatatcgaa ttcctgcagc cc                       42

<210> SEQ ID NO 28
<211> LENGTH: 46
<212> TYPE: DNA
<213> ORGANISM: Artificial Sequence
<220> FEATURE:
<223> OTHER INFORMATION: nucleotide seqeunce of Forward primer

<400> SEQUENCE: 28
ctaggtcgac ggtatcgata agcttgatat cgaattcctg cagccc                   46

<210> SEQ ID NO 29
<211> LENGTH: 46
<212> TYPE: DNA
<213> ORGANISM: Artificial Sequence
<220> FEATURE:
<223> OTHER INFORMATION: nucleotide seqeunce of Reverse primer

<400> SEQUENCE: 29
ctaggggctg caggaattcg atatcaagct tatcgatacc gtcgac                   46

<210> SEQ ID NO 30
<211> LENGTH: 40
<212> TYPE: DNA
<213> ORGANISM: Artificial Sequence
<220> FEATURE:
<223> OTHER INFORMATION: Forward primer for amplifying WPRE

<400> SEQUENCE: 30
ggtggtttaa ttaaaatcaa cctctggatt acaaaatttg                          40

<210> SEQ ID NO 31
<211> LENGTH: 30
<212> TYPE: DNA
<213> ORGANISM: Artificial Sequence
<220> FEATURE:
<223> OTHER INFORMATION: Reverse primer for amplifying WPRE

<400> SEQUENCE: 31
ggtggtgtta acgacaacac cacggaattg                                     30

<210> SEQ ID NO 32
<211> LENGTH: 38
<212> TYPE: DNA
<213> ORGANISM: Artificial Sequence
<220> FEATURE:
<223> OTHER INFORMATION: Forward primer for amplifying hrGFP

<400> SEQUENCE: 32
ggtggtgcta gcgccaccat ggtgagcaag cagatcct                            38
```

-continued

```
<210> SEQ ID NO 33
<211> LENGTH: 32
<212> TYPE: DNA
<213> ORGANISM: Artificial Sequence
<220> FEATURE:
<223> OTHER INFORMATION: Reverse primer for amplifying hrGFP

<400> SEQUENCE: 33
ggtggtttaa ttaacaccca ctcgtgcagg ct                                          32
```

METHOD FOR DELIVERY OF BIOLOGICAL MOLECULE TO NERVOUS TISSUE

CROSS REFERENCE TO RELATED APPLICATIONS

This application is a Continuation-in-Part of U.S. application Ser. No. 15/754,849 filed Feb. 23, 2018, which is a National Stage application under 35 U.S.C. § 371 of International Application No. PCT/KR2016/010480, filed on Sep. 20, 2016, and claims the benefit of Korean Application No. 10-2015-0133349 filed Sep. 21, 2015, the disclosures of which are incorporated herein by reference in their entireties.

TECHNICAL FIELD

The present invention relates to a method for delivery of a biological molecule to a nervous tissue. More particularly, the present invention relates to a method of delivering a biological molecule to a nervous tissue protected by the brain-blood barrier or meninges.

BACKGROUND ART

The delivery of a therapeutic agent to a target site is a very important factor in the development of therapeutic agents. In particular, with regard to neurological treatment, the nerves of the brain or spinal cord are surrounded by membranes such as the brain-blood barrier (BBB), meninges, etc., making it difficult to deliver therapeutic agents thereto. In order to pass through the BBB or meninges, the therapeutic agent should be a very small low molecular substance and have a physical property of good membrane permeability such as a synthetic drug. Accordingly, in order to deliver a macromolecular genetic material to the nerve tissue, it is necessary to delivery it directly to the treatment site, but this could lead to a direct nerve injury, and thus it is difficult to develop a biopharmaceutical agent for delivery using a genetic material.

Recently, Periphagen Holdings has developed a gene therapeutic agent, which is a herpes simplex virus (HSV) loaded with a gene that produces an opioid peptide, enkephalin. However, the problem of poor analgesic effect was found in clinical trials, and the trial was halted at phase 2. Specifically, HSV can deliver a gene to the peripheral nerve even when administered subcutaneously because HSV has a tropism to the nervous tissue, but there is a problem of a low efficiency of gene delivery. In addition, there is an example of delivering genetic material to the nervous system non-invasively through intravascular injection using adeno-associated virus. However, this is not a generally available method because the transduction efficiency is relatively low and high viral load must be used.

Therefore, there is a need to develop a method of administration that can safely and effectively deliver a biological molecule to the nervous tissue.

DISCLOSURE OF INVENTION

Technical Problem

Accordingly, the inventors of the present invention have endeavored to find a method for efficient delivery of a biological molecule to a nervous tissue, and have found that a biological molecule can be delivered to a nervous tissue safely and efficiently when administered to a space between the inside of an intervertebral foramen and the dura mater surrounding the spinal cord and spinal nerve.

Solution to Problem

In one aspect, the present invention provides a method for delivery of a biological molecule to a nervous tissue, which comprises injecting the biological molecule into a space between the inside of an intervertebral foramen and the dura mater surrounding the spinal cord and spinal nerve.

In another aspect, the present invention provides a method for relieving or treating pain, comprising injecting a composition comprising a gene encoding glutamate decarboxylase (GAD), a gene encoding interleukin-10 (IL-10), or a gene encoding a combination of GAD and IL-10 to a space between the inside of an intervertebral foramen and the dura mater surrounding the spinal cord and spinal nerve.

Advantageous Effects of Invention

The method for delivery of the present invention allows delivery of a biological molecule to a nervous tissue with high efficiency. In addition, the delivery of a biological molecule to a nervous tissue by the delivery method of the present invention is safe since it has lower side effects such as nervous damage than a method of administering a biological molecule directly to a nervous tissue.

BRIEF DESCRIPTION OF DRAWINGS

FIG. 1 shows a vector map of the plasmid pAAV-hGAD65 used for the production of recombinant adeno-associated virus.

FIG. 2 shows a vector map of the plasmid pAAV-rIL-10 used for the production of recombinant adeno-associated virus.

FIG. 3 shows a vector map of the plasmid pAAV-rIL-4 used for the production of recombinant adeno-associated virus.

FIG. 4 is a diagram confirming the expression level of each protein by Western blot, where adeno-associated viruses respectively loaded with GAD65, IL-10 and IL-4 genes were prepared, and then 293T cells, a human embryonic kidney cell line, were treated with the viruses, and cells or culture media were collected after 48 hours.

FIG. 5 illustrates the expression of GABA by a recombinant adeno-associated virus AAV-hGAD65, which is a diagram showing GABA levels in the media measured by ELISA, where 293T cells, a human embryonic kidney cell line, were treated with AAV-GAD65, and the culture media were collected after 48 hours. Duplicated samples were prepared separately for each experiment group, and the bar represents the value of GABA for each sample.

FIG. 6 shows the results of comparing the efficacies of co-administration of AAV-GAD65 and AAV-IL-10 in animal behavior analysis as compared to gabapentin used as a neuropathic pain reliever in the market.

FIG. 7 illustrates the efficacies of AAV-GAD65 and AAV-IL-10 depending on composition ratios thereof. It shows the pain-relieving effects in animal behavior analysis with the composition ratios of AAV-IL-10 to AAV-GAD of 1:1, 1:5, or 1:30.

FIG. 8 illustrates the pain-relieving effects when AAV-GAD65 and AAV-IL-10 were co-administered at the composition ratios of 1:10 or 1:30 by transforaminal epidural injection.

FIG. 9 shows the results of comparing the efficacies of AAV-GAD65 and AAV-IL-10 with AAV-GAD65 and AAV-IL-4 which illustrates excellent pain-relieving effects in animal behavior analysis when IL-10 and IL-4, known to have antiinflammatory effect, were respectively combined with GAD65 for use.

FIG. 10A illustrates the result of qPCR analysis of cell lysates of the Hela cell line transfected with AAV5-Flag-hGAD65 used in an animal experiment using rats, which shows that the transfected Hela cell line expresses Flag.

FIG. 10B illustrates the result of Western blot analysis of cell lysates of the Hela cell line transfected with AAV5-Flag-hGAD65 used in an animal experiment using rats, which shows that the transfected Hela cell line expresses Flag.

FIG. 10C illustrates the result of Western blot analysis of cell lysates of the Hela cell line transfected with AAV5-Flag-hGAD65 used in an animal experiment using dogs, which shows that the transfected Hela cell line expresses Flag.

FIG. 10D illustrates the result of Western blot analysis of cell lysates of the Hela cell line transfected with AAV5-hGAD65 used in an animal experiment using micro-pigs, which shows that the transfected Hela cell line expresses GAD65.

FIG. 10E illustrates the result of ELISA analysis of cell culture of a HeLa cell line transfected with AAV5-hGDNF/hIL-10, which shows that the transfected. HeLa cell line expresses IL-10 and GDNF.

FIG. 11 provides the results of fluorescence microscopy examination of the expression of GFP protein after treating 293T cell line with a pAAV-GFP.

FIG. 12 provides the result of H & E staining of the nerve tissue of a rat model administered with AAV5-hGAD65 through DRG injection, by which it was determined whether cytotoxicity was exhibited in the nerve tissue.

FIG. 13A provides the result of immunohistochemical staining of the nerve tissue of a rat model administered with AAV5-Flag-hGAD65 by transforaminal epidural injection, which shows that AAV5-Flag-hGAD65 was delivered to and expressed in the nerve tissue.

FIG. 13B provides the result of H & E staining of the nerve tissue of a rat model administered with AAV5-hGAD65 by transforaminal epidural injection, by which it was determined whether cytotoxicity is exhibited in the nerve tissue.

FIG. 14 provides the result of immunohistochemical staining of the nerve tissue of a rat model administered with Ad-GFP by transforaminal epidural injection, which shows that Ad-GFP was delivered to and expressed in the nerve tissue.

FIG. 15 provides the result of immunohistochemical staining of the nerve tissue of a rat model administered with the pAAV-GFP plasmid by transforaminal epidural injection, which shows that the pAAV-GFP plasmid was delivered to and expressed in the nerve tissue.

FIG. 16 illustrates the process of administering AAV5-Flag-hGAD65 to a dog model by transforaminal epidural injection.

FIG. 17 illustrates the process of administering AAV5-hGAD65 and AAV5-hGDNF/hIL-10 to a micro-pig model by transforaminal epidural injection.

BEST MODE FOR CARRYING OUT THE INVENTION

Hereinafter, the present invention will be described in detail.

In one aspect, the invention provides a method for delivery of a biological molecule to a nervous tissue, which comprises injecting the biological molecule into the space between the inside of the intervertebral foramen and the dura mater surrounding the spinal cord and spinal nerve.

The above intervertebral foramen is a space between a body of vertebra and a vertebral arch through which a spinal nerve emerges from the spinal cord.

The above nervous tissue may be protected by the brain-blood barrier or meninges. Herein, the nervous tissue may be a tissue of brain including cerebrum, cerebellum, pons, midbrain, or medulla oblongata. In addition, the nervous tissue may be a dorsal root ganglion (DRG) of the spinal cord, or a spinal nerve. Specifically, the nervous tissue may be a dorsal root ganglion.

The cerebrum, cerebellum, pons, midbrain, and medulla oblongata are the sub-organs constituting the brain, and conduct exercise, sensory, language, memory, and high level mental functions, and maintain environments necessary for survival such as arousal, maintenance of homeostasis, regulation of body metabolism, etc. The brain has abundant vascular tissues, and the cerebral blood vessels have a structure called blood brain barrier to protect the brain from toxic substances.

The blood-brain barrier is a barrier separating the cerebrospinal fluid and blood, and has a high selective permeability, which acts to isolate the central nervous system such as the brain from the pathogens which can be delivered via blood such as bacteria, etc., or potential pathogens in the blood. When a functional disorder takes place in the brain surrounded by the blood brain barrier, it is difficult to deliver a therapeutic agent to treat the disorder.

On the other hand, the dorsal root ganglion, also called spinal ganglion, refers to a pair of left and right nerve bundles from spinal nerves. When a genetic therapeutic agent is delivered to the DRG, a method of direct administration to the DRG is used. Such method may induce physical injury to the nerve tissues themselves, and may be accompanied by fatal risk such as infective encephalomeningitis. Specifically, it is difficult to deliver a therapeutic agent to the nerve tissue of the spinal cord via an administration route other than direct administration since the nerve tissues are surrounded by meninges and thus separated from tissues of the outside. The meninges are composed of dura mater, arachnoid mater, and pia mater.

The dura mater is the thickest membrane among the membranes constituting the meninges, and is mainly composed of collagen. The arachnoid mater is in contact with the dura mater and has a portion made of fibers and collagens to protect the brain and spinal cord from impact. Also, the arachnoid mater forms a space called a subarachnoid space between the arachnoid mater and the pia mater, which provides the permeation rates and selectivity for delivery of a therapeutic agent to the nerve tissue. Subarachnoid space is formed between the arachnoid mater and pia mater, in which cerebrospinal fluid is present. The pia mater is the innermost membrane, that surrounds the spinal cord and brain. In addition, the pia mater contains blood vessels that supply oxygen and nutrients to the spinal cord. Each membrane has different constituents, and thus difficult to permeate.

Therefore, the present inventors have investigated to find a suitable administration route for delivering a biological molecule to a nervous tissue protected by the brain-blood barrier or meninges, and found that if the biological molecule is injected into a space between the inside of an intervertebral foramen and the dura mater surrounding the spinal cord and spinal nerve, the biological molecule is delivered to the nerve tissue.

Until now, there has been no research or expectation that a viral or non-viral biological molecule will be delivered to nerve tissues by passing through meninges when injected into a space between the inside of an intervertebral foramen and the dura mater. In addition, it has been reported in previous studies that the biggest barrier of transmeningeal permeation is arachnoid mater (*Anesthesiology* 11 1991, Vol. 75, 827-832) Cerebrospianl fluid is present in the subarachnoid space, which acts as a barrier to the movement of materials. That is, moving to the subarachnoid space from the subdural space means passing of macromolecules through a membrane that can hold liquid such as cerebrospinal fluid.

Therefore, it is unpredictable that macromolecules such as biological molecule can carry out transmingeal permeation, which has been first identified by the present inventors and thus we have completed the present invention.

The biological molecule may be a therapeutic agent. In addition, the biological molecule may be a nucleic acid or a peptide. The nucleic acid may be in the form of RNA or DNA.

The RNA may be in the form of mRNA, miRNA, siRNA or shRNA, but is not limited thereto.

The mRNA is RNA that transfers the genetic information of DNA in the nucleus of the cell to the ribosome in the cytoplasm. The mRNA may be one encoding an active protein. The active protein may be a protein used for treating neurological disorders or for relieving neuropathic pain. Specifically, the active protein may be an enzyme, a neurotrophic factor, or a cytokine, but is not limited thereto.

The enzyme may be one used for the treating neurological disorders or relieving neuropathic pain relief. In one embodiment, the enzyme may be glutamate decarboxylase (GAD).

The neurotrophic factor may be one selected from the group consisting of NGF (nerve growth factor), BDNF (brain derived neurotrophic factor), NT-3 (neurotrophin 3), NT-4 (neurotrophin 4), GDNF (Glial cell line-derived neurotrophic factor), Artemin, Neurturin, Persephin, Ephrins (A1, A2, A3, A4, A5, B1, B2, B3), CNTF (Ciliary neurotrophic factor), GMF (Glia maturation factor), IGF-1 (Insulin-like growth factor 1), Neuregulins (1, 2, 3, 4), PACAP (Pituitary adenylate cyclase-activating peptide), VEGF (Vascular endothelial growth factor) or combinations thereof.

In one embodiment, the neurotrophic factor may be GDNF. The GDNF refers to a protein that constitutes the GDNF ligand family. The GDNF ligand family consists of GDNF, neurturin (NRTN), artemin (ARTN), and persephin (PSPN). In addition, the GDNF is a protein that promotes the survival of many kinds of neurons and transmits signals through the GFRα1 receptor. The GDNF may be a protein derived from, but is not limited to, a human, a rat, a dog, a cat, or a horse. Specifically, it may be a human-derived protein, and specific examples thereof can be encoded by the nucleotide sequence of NCBI NM_199231.2.

The cytokine may be one selected from the group consisting of IL-1α, IL-1β, IL-2, IL-3, IL-4, IL-5, IL-6, IL-7, IL-8, IL-9, IL-10, IL-11, IL-12, IL-13, IL-15, IL-16, IL-17, IL-18, IL-19, IL-20, IL-21, IL-22, IL-23, IL-25, GM-SCF, G-CSF, M-CSF, SLF, TNF-α, TNF-β, IFNα, IFNβ, IFNγ, TGFβ, LIF, Eta-1, Oncostatin M, and combinations thereof. In one embodiment, the cytokine may be IL-10 or IL-4.

The miRNA, siRNA or shRNA may have a sequence complementary to the nucleic acid encoding the target protein. For the diseases caused by overexpression of a specific protein in the nervous tissue, a nervous disease can be treated or neural pain can be relieved by delivering miRNA, siRNA or shRNA targeting the overexpressed specific protein to the nervous tissue to inhibit overexpression of the target protein.

The miRNA (microRNA) is a small RNA that plays a role of controlling gene expression in an organism. Specifically, miRNA is RNA consisting of about 22 nucleotides which is found in plants, animals, viruses, etc., and functions in RNA silencing and post transcriptional regulation of gene expression, and the like. miRNAs function via base-pairing with complementary sequences within mRNA molecules. As a result, these mRNA molecules are regulated by cleavage of the mRNA strand into two pieces, by shortening the poly A tail of mRNA to destabilize mRNA, or by reducing the efficiency of mRNA by ribosome.

The siRNA (small interfering RNA), also called silencing RNA, inhibits the production of a specific protein by inhibiting gene expression. In addition, siRNA composed of 21 to 23 nucleotides forms base pairs to match the complementary sequence of the mRNA so that the mRNA forms double-stranded RNA. The formed double-stranded RNA removes mRNA from the cell as it is degraded.

The shRNA (short hairpin RNA) is an artificial RNA molecule having a hairpin structure used for silencing target gene expression through RNA interference. The shRNA is delivered into a cell through a plasmid vector or a viral vector and expressed. The hairpin structure of the shRNA is cleaved by Dicer and acts on RNA silencing like siRNA. ShRNAs are advantageous for RNA interference in that they are degraded relatively slowly in the cell.

The mRNA, miRNA, siRNA or shRNA may be embedded in a carrier. Herein, the carrier may be any one selected from the group consisting of a liposome, a cationic polymer, a micelle, lipid nanoparticles, and combinations thereof, but is not limited thereto.

The term "liposome" as used herein refers to a small spherical vesicle which is formed when a molecule having both hydrophilic portion and hydrophilic portion simultaneously in the molecule such as a phospholipid is suspended in an aqueous solution, which leads to a bilayer formation due to the hydrophilic portion and hydrophilic portion. Liposome can be used as a mediator of delivery of a genetic material such as DNA, mRNA, etc.

The term "cationic polymer" as used herein refers to a cationic lipid or a polymer compound, which forms a complex with DNA by ionic bonding and is delivered into a cell.

The term "micelle" as used herein refers to a thermodynamically stable colloidal aggregate which is formed when molecules consisting of a polar group and a nonpolar hydrophobic group, such as surfactants or lipid molecules, are aggregated in a solution by a van der Waals force, etc. In addition, a micelle containing DNA, mRNA, and the like can be used as a mediator of delivery of a genetic material.

The term "lipid nanoparticle" as used herein refers to a preparation in which a drug is contained in nano-sized microparticles made of a solid lipid instead of a liquid lipid.

The DNA may encode an active protein or shRNA, and the active protein is the same as described above.

The DNA may be one loaded in a vector. The vector may be, but is not limited to, a viral vector, a plasmid, a cosmid, a bacterial artificial chromosome, a yeast artificial chromosome, or a human artificial chromosome. In one embodiment, the vector may be a viral vector.

The viral vector may be any one selected from the group consisting of adenovirus, adeno-associated virus, herpesvirus, lentivirus, retrovirus, poxvirus, and combinations thereof. In one embodiment, the viral vector may be an adeno-associated virus. The adeno-associated virus is suitable for gene delivery because it can infect non-dividing cells and infect various kinds of cells.

The term "plasmid" as used herein refers to a circular DNA fragment separated from a chromosome of a bacterium. The plasmid has no gene essential for bacterial survival, but may contain genes essential for resistance to specific antibiotics and interbacterial gene exchange. In addition, the plasmid may contain a selectable marker.

The cosmid is a plasmid containing a fragment of bacteriophage λ DNA having cos (cohesive end site) containing elements necessary for packaging DNA into lambda particles. The cosmid is usually used to clone large DNA fragments between 28 kb and 45 Kb.

The bacterial artificial chromosome can replicate an insertion size of up to 350 kb. Bacterial artificial chromosomes are maintained in a single copy number per cell in *E. coli*. In addition, bacterial artificial chromosomes are based on the F plasmid, and another artificial chromosome called PAC (P1-derived artificial chromosome) is based on the P1 phage.

The human artificial chromosome may be potentially useful as a gene delivery vector for gene delivery into human cells and as a tool for expression studies and human chromosome function determination. Human artificial chromosomes can carry very large DNA fragments, and there is no such problem as the limited replication ability of other vectors. In addition, the human artificial chromosome can avoid the insertion mutation caused by the integration into the host chromosome by the virus.

The peptide may be an active protein. The active protein is the same as described above. In addition, the peptide may be embedded in a carrier. The carrier is the same as described above.

When the biological molecule is a viral vector, they may be administered in an amount of $1.0 \times 10^6$ to $1.0 \times 10^{14}$ vg (viral genome) on an adult basis, but is not limited thereto. In addition, when there are two types of virus to be administered, each type of virus can be administered in an amount of $5.0 \times 10^5$ to $5.0 \times 10^{13}$ vg. If there are three types of virus to be administered, each type of virus can be administered in an amount of $3.0 \times 10^5$ to $3.0 \times 10^{13}$ vg.

When the biological molecule is comprised in a carrier, they can be administered at a concentration of 0.01 μg/1 ml to 10 mg/l ml per day on an adult basis, but is not limited thereto. Also, when the biological molecules comprise a plasmid vector, the dosage may be 0.1 ml, 1 ml, 2 ml, 3 ml, 4 ml, 5 ml, 6 ml, 7 ml, 8 ml, 9 ml, 10 ml or more, including all values and ranges between them.

The number of administrations when the biological molecule is a viral vector, may be 1 or more, or 1 to 10, but is not limited thereto. And in the case of repeated administration, it may be administered at the interval of 1 day to 1 month, or 1 month to 1 year. When the biological molecule is comprised in a carrier, the number of administrations may be 1 or more, or 1 to 10, but is not limited thereto. And in the case of repeated administration, it may be administered at the interval of 12 to 24 hours or 1 to 14 days.

The biological molecules may be administered with a physiologically acceptable additive. In addition, the biological molecules may be administered with a suitable excipient and diluent conventionally used in the manufacture. In addition, it can be formulated for use in the form of a tablet, a suspension, an emulsion, a syrup, an aerosol, an external preparation, or an injection according to a conventional method. Specifically, the biological molecules may be in the form of an injection. The suitable formulation known in the art may be one of those listed in Remington's Pharmaceutical Science (1985).

In another aspect, the present invention provides a method for relieving or treating pain, which comprises injecting a composition comprising a gene encoding glutamate decarboxylase (GAD), a gene encoding an anti-inflammatory cytokine, or a gene encoding a combination thereof into a space between the inside of an intervertebral foramen and the dura mater surrounding the spinal cord and spinal nerve.

The above gene may be loaded in a viral vector, a plasmid, a cosmid, a bacterial artificial chromosome, a yeast artificial chromosome, or a human artificial chromosome. Herein, the gene may be in the form of DNA.

The viral vector may be any one selected from the group consisting of adenovirus, adeno-associated virus, herpesvirus, lentivirus, retrovirus, poxvirus, and combinations thereof.

Also, the above gene may be embedded in any one carrier selected from the group consisting of a liposome, a cationic polymer, a micelle, lipid nanoparticles, and combinations thereof, but is not limited thereto. Here, the gene may be in the form of mRNA or a vector. The above vector is the same as described above.

A carrier containing a gene encoding GAD according to the present invention (e.g., a first vector) and a carrier containing a gene encoding IL-10 (e.g., a second vector) may have a virus titer-based mixing ratio per unit volume of 1:1 to 1:100, 1:1 to 1:80, 1:1 to 1:60, 1:1 to 1:40, 1:1 to 1:20, 1:1 to 1:10, 1:3 to 1:100, 1:3 to 1:80, 1:3 to 1:60, 1:3 to 1:40, 1:3 to 1:20, or 1:3 to 1:10, more preferably 1:1 to 1:50, and most preferably 1:5 to 1:30.

The first vector and the second vector may be adeno-associated viruses. The adeno-associated virus is not limited to a specific serotype, and preferably, it may be any one of AAV1 to AAV5.

The GAD is an enzyme that decarboxylates glutamate to produce GABA (gamma-aminobutyric acid). The GAD encoding gene applicable to the present invention may be GAD65 or GAD67, which are two isoforms. The GAD65 may be a human or rat protein, and specific examples thereof may be composed of the amino acid sequence of the NCBI accession No. 1. And it may be encoded by the nucleotide sequence of SEQ ID NO: 2 or SEQ ID NO: 3. The GAD67 may be a human or rat protein. Specific examples of which may be composed by the amino acid sequence of the NCBI accession No. 4 of NM_000817, and may be encoded by the nucleotide sequence of SEQ ID NO: 5.

The IL-10 is one of the anti-inflammatory cytokines and is also known as a cytokine synthesis inhibitory factor (CSIF). IL-10 belongs to the class II cytokine and is a homodimer consisting of two subunits of 178 amino acids in length. IL-10 acts to inhibit the activity of NK (natural killer) cells, B cells, T cells, macrophages or mast cells in the immune response, and forms a complex with the IL-10 receptor and participates in signal transduction. IL-10 can be a human or rat protein, specific examples of which include NCBI accession no. SEQ ID NO: 6 of NM_012854 or NCBI accession no. 9 of SEQ ID NO: 9, or may be encoded by the nucleotide sequence of SEQ ID NO: 7, SEQ ID NO: 8, or SEQ ID NO: 10.

The nucleotide sequence of the GAD-encoding gene and/or the IL-10 encoding gene includes variants thereof, which may be a nucleotide sequence modified by optimized codons for rat or human. Specifically, a base sequence having at least 60%, at least 70%, at least 80%, at least 90%, preferably at least 95% sequence identity with the nucleotide sequence of the coding sequence according to the present invention is included, "homology" is determined by comparing the comparison region with two optimally arranged sequences, and some of the base sequences in the comparison region are added to the reference sequence (without addition or deletion) of the optimal sequence of the two sequences (i.e., a gap).

When the composition comprises a viral vector, it may be administered in an amount of $1.0 \times 10^6$ to $1.0 \times 10^{14}$ viral genome (vg) on an adult basis, but is not limited thereto. In addition, when there are two viral types to be administered, each type of virus can be administered in an amount of $5.0 \times 10^5$ to $5.0 \times 10^{13}$ vg. If there are three types of viruses to be administered, each type of virus can be administered in an amount of $3.0 \times 10^5$ to $3.0 \times 10^{13}$ vg.

When the composition contains a carrier, it may be administered at a concentration of 0.01 µg/1 ml to 10 mg/l ml on an adult basis, but is not limited thereto. In addition, when the composition comprises a carrier, the dose may be 0.1 ml, 1 ml, 2 ml, 3 ml, 4 ml, 5 ml, 6 ml, 7 ml, 8 ml, 9 ml, 10 ml or more, including all values and ranges between them.

The number of administration may be, but is not limited to, once or more, or 1 to 10 times, when the composition contains a viral vector. In the case of repeated administration, it may be administered at the intervals of 1 day to 1 month, or 1 month to 1 year.

When the composition contains a carrier, it may be administered, but is not limited to, once or more, or 1 to 10 times, when the composition contains a carrier. In the case of repeated administration, it may be administered at the intervals of once or more, but not limited to, 12 to 24 hours, or 1 to 14 days.

The above method may further comprise, prior to the administering step, identifying a patient as the patient in need of relieving or treating pain.

The composition may further comprise a physiologically acceptable carrier. In addition, the therapeutic agent may further comprise a suitable excipient and diluent conventionally used in the manufacture. In addition, it can be formulated for use in the form of a tablet, a suspension, an emulsion, a syrup, an aerosol, an external preparation, or an injection according to a conventional method. Specifically, the pharmaceutical composition may be in the form of an injection. The suitable formulation known in the art may be one of those listed in Remington's Pharmaceutical Science (1985).

The subject for administration may be a mammal including a human, or a cell and/or tissue isolated from a mammal including a human. Also, the subject may be a non-human animal, and the term "non-human animal" refers to all vertebrates such as mammals or non-mammals, for example, primates except humans, sheep, dogs, cats, horses, cows, chickens, amphibians, reptiles, etc.

The term "neurological disorder" as used herein refers to a disorder in which dysfunction of the brain, spinal cord, or nerves occurs. Specifically, the neurological disorders include brain tumors (glioma), cerebral infarction, hypertensive cerebral hemorrhage, cerebral contusion, cerebral arteriovenous malformation, brain abscess, encephalitis, hydrocephalus, epilepsy, concussion, cerebral palsy, Parkinson's disease, Alzheimer's disease, spinal cord tumor, spinal cord ateriovenous malformation or spinal cord infarction, but are not limited thereto.

As used herein, the term "pain" may be an inflammatory pain associated with tissue damage and immune cell infiltration, or a pathological pain which is a disease state induced by damage to the nervous system or its abnormal function (e.g. fibromyalgia, irritable bowel syndrome, dysfunctional pain such as tension headache). The pain may be nociceptive pain, psychogenic pain, inflammatory pain, pathological pain, neuropathic pain, cancer pain, postoperative pain, trigeminal neuralgia pain, idiopathic pain, diabetic neuropathic pain, or migraine.

Also, the pain may include back pain distinguished anatomically, such as: neck pain, middle back pain, lower back pain, or tailbone pain. In addition, the pain may include pain such as neuropathic pain, migraine, etc. Neuropathic pain can result from damage or diseases that affect the somatosensory system. Neuropathic pain may be associated with an abnormal sensation called dysesthesia, and with allodynia in which pain sensation is evoked even with painless stimulation. Also, the neuropathic pain may also be a continuous and/or intermittent (seizure) factor. The latter is linked to electric shock in the figurative sense. General property may include being hot or cold, pins and needles, numbness, and itching.

In contrast, nociceptive pain is often expressed as "ache". In addition, migraine is a chronic disorder that is associated with a number of autonomic nervous system symptoms and causes headaches of ordinary to severe intensities. The precise mechanisms of these migraines have not been clarified yet. The basic theory is related to the increased excitability of the cerebral cortex and the abnormal regulation of pain nerve cells in the trigeminal nucleus of the brain stem.

Also, the pain may be at least one selected from the group consisting of neuropathic pain, cancer pain, postoperative pain, trigeminal neuralgia, idiopathic pain, diabetic neuropathic pain, migraine, etc. As another specific example, the pain may not be a muscle spasm associated with lumbago.

The term "transforaminal epidural injection" refers to a method of injecting a drug into a space between the inside of an intervertebral foramen and the dura mater surrounding the spinal cord and spinal nerve.

MODE FOR THE INVENTION

Hereinafter, the present invention is explained in detail by Examples, but the following Examples are intended to further illustrate the present invention without limiting its scope.

<Example 1> Preparation and Property Analysis of Recombinant Adeno-Associated Viruses A. Preparation of pAAV-hGAD65

To prepare pAAV-hGAD65 of FIG. 1, the CMV promoter region of pJDK-rGAD65 [Lee B et al., Gene Ther, 12: 1215-1222 (2005)] was amplified by PCR and then introduced into pGEM-T (Promega, USA), to prepare pGEM-T-CMV. The primer sequences used for the amplification of CMV promoter are as follows.

F-JDK (SEQ ID NO: 16):
5'-TTCGGCCGTCGAGGAGCTTGGCCCATTG-3'

R-JDK (SEQ ID NO: 17):
5'-GACGTCGACCTAGCTAGCGAATTCGGGGCCGCGGAG-3'

The GAD65 gene was prepared by codon-optimization to be suitable for humans based on the human GAD65 sequence having the amino acid sequence of SEQ ID NO: 1 (NCBI NM_000818) and synthesizing the base sequence of SEQ ID NO: 3 (Bioneer, Korea). The hGAD65 gene introduced into pGEM-T was treated with NheI and SalI to obtain a 1.7 Kb DNA fragment, which was ligated to a 3.7 Kb DNA fragment obtained by treating pGEM-T-CMV with NheI and SalI, to complete the preparation of pGEM-T-CMV-hGAD65.

SV40 pA was amplified by conducting PCR using pCI (Invitrogen, USA) as a template, followed by treatment with ClaI and SalI, to obtain a 222 bp DNA fragment. The above fragment was ligated to a 5.4 Kb DNA fragment prepared by cutting pGEM-T-CMV-hGAD65 with ClaI and SalI, to finally prepare pGEM-T-CMV-hGAD65-SV40 pA. The primer sequences used for the amplification of SV40 pA are as follows.

F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'

The ampicillin-resistance gene in pAAV-MCS (Agilent, USA) was replaced with kanamycin-resistance gene for the preparation of adeno-associated virus vectors. The kanamycin-resistance gene was amplified by PCR using pET-28(a) (Novagen, USA) as a template, and the amplified 816 bp kanamycin-resistance gene was ligated to pGEM-T, to prepare pGEM-T-Kan$^r$. The primer sequences used for the amplification of kanamycin-resistance gene are as follows.

F-Kan (SEQ ID NO: 20):
5'-AGGCGCCATGAGCCATATTCAACGGGAA-3'

R-Kan (SEQ ID NO: 21):
5'-TTCATGATTAGAAAAACTCATCGAGCATC-3'

For the introduction of the kanamycin-resistance gene, SpeI and EcoRV sites were respectively generated at the front and back of the ampicillin-resistance gene in pAAV-MCS by mutagenesis, and treated with SpeI and EcoRV, which was then ligated to the DNA fragment obtained by cutting the pGEM-T-Kan$^r$ prepared above with NheI and EcoRV, to prepare pAAV-MCS-Kan$^r$.

The prepared pAAV-MCS-Kan$^r$ was treated with NotI and BamHI, which was then ligated to a 2.7 Kb DNA fragment obtained by cutting pGEM-T-CMV-hGAD65-SV40 pA with EagI and PvuI, to prepare pssAAV-GAD65.

In order to introduce the GAD65 expression cassette into pVAX1 (Invitrogen, USA), BamHI site was generated at the back of bGHpA by mutagenesis, which was then cut with MluI and NheI, to prepare DNA fragments. The LITR and CMV promoter regions were amplified by PCR using the pssAAV-GAD65 as a template, and cloned into pGEM-T easy (Promega, USA), which were then cut with AscI and NheI, and ligated to the pVAX1 vector prepared above, to prepare pVAX1-LITR-CMV. The primer sequences used for the amplification of LITR and CMV promoter regions are as follows.

F-ITR (SEQ ID NO: 22):
5'-ATGGCGCGCCCCTGGCCTTTTGCTGGCC-3'

R-JDK (SEQ ID NO: 17):
5'-GACGTCGACCTAGCTAGCGAATTCGGGGCCGCGGAG-3'

The pVAX1-LITR-CMV was prepared as a DNA fragment by cutting with NotI and NheI, and ligated to the DNA fragment prepared by cutting the pssAAV-GAD65 with EagI and NheI, to prepare pVAX1-LITR-CMV-hGAD65-SV40 pA.

The pVAX1-LITR-CMV-hGAD65-SV40 pA was cut with HpaI and BamHI, and then ligated to the DNA fragments obtained by treating the pGEM-T easy-SV40 pA-RITR, which had been amplified by PCR using pssAAV-GAD65 as a template and cloned into pGEM-T easy, with HpaI and BamHI, to complete pVAX1-LITR-CMV-hGAD65-SV40 pA-RITR (hereinafter, abbreviated as "pAAV-GAD65"). The primer sequences used for the amplification of SV40 pA and RITR regions are as follows.

F-SV40pA (SEQ ID NO: 18):
5'-CCATCGATCAGACATGATAAGATACATTGATGAG-3'

R-ITR (SEQ ID NO: 23):
5'-ATGGATCCGCTAGTAAATACCGCATCAG-3'

The vector map of pAAV-hGAD65 is shown in FIG. 1.

B. Preparation of pAAV-rIL-10 pAAV-rIL-10 was prepared by a similar method to pAAV-hGAD65. Rat IL-10 gene was prepared by codon-optimization to be suitable for rats based on rat-derived base sequence (NCBI NM_012854) having the amino acid sequence of SEQ ID NO: 6 and synthesizing a gene having the base sequence of SEQ ID NO: 8 (Bioneer, Korea). The rIL-10 genes were amplified by PCR using the rat IL-10 genes introduced into pGEM-T easy as a template, and then treated with NheI and SalI to obtain a 0.5 Kb DNA fragment, which was then ligated to a 3.7 Kb DNA fragment obtained by cutting the pGEM-T-CMV with NheI and SalI, to prepare pGEM-T-CMV-rIL-10. The primer sequences used for the amplification of rIL10 is as follows.

F-rIL-10 (SEQ ID NO: 24):
5'-CCGCTAGCGCCACCATGCCT-3'

R-rIL-10 (SEQ ID NO: 25):
5'-GACGTCGACGCCATCGATGGCTTAATTAATCAATTCTTC-3'

SV40 pA was amplified by conducting PCR using pCI as a template, followed by treatment with NotI and SalI to obtain a 222 bp DNA fragment. The above fragment was ligated to a 4.2 Kb DNA fragment prepared by cutting pGEM-T-CMV-rIL-10 prepared above with ClaI and SalI, to prepare pGEM-T-CMV-rIL-10-SV40 pA. The primer sequences used for the amplification of SV40 pA are as follows.

F-SV40pA (SEQ ID NO: 18):
5'-CCATCGATCAGACATGATAAGATACATTGATGAG-3'

R-SV40pA (SEQ ID NO: 19):
5'-GACGTCGACGCGGCCGCTACCACATTTGTAGAGGTTTTACTTG-3'

A 1.6 Kb DNA fragment was obtained by treating pGEM-T-CMV-rIL-10-SV40 pA with EagI, and then ligated to the DNA fragment prepared by treating pAAV-MCS-Kan$^r$ with NotI and BamHI, to prepare pssAAV-CMV-rIL-10-SV40 pA (hereinafter, abbreviated as "pAAV-rIL-10"). The vector map of pAAV-rIL-10 is shown in FIG. 2.

C. Preparation of pAAV-rIL-4

The rat IL-4 gene was prepared by codon-optimization to be suitable for rats based on the rat-derived base sequence (NCBI NM_201270) having the amino acid sequence of SEQ ID NO: 11 and synthesizing a gene having the base sequence of SEQ ID NO: 13 (Bioneer, Korea). The rIL-4 genes introduced into pGEM-B1 (Bioneer, Korea) were treated with NheI and NotI to obtain a 0.5 Kb DNA fragment. The above fragment was ligated to a 3 Kb DNA fragment prepared by treating pAAV-hGAD65 with NheI and NotI, to prepare pssAAV-CMV-rIL-4-SV40 pA (hereinafter, abbreviated as "pAAV-rIL-4"). The vector map of pAAV-rIL-4 is shown in FIG. 3.

D. Property Analysis of Recombinant Adeno-Associated Viruses

The three types of plasmids (pAAV-hGAD65, pAAV-rIL-10 and pAAV-rIL-4) prepared above were respectively transfected into 293T cells, a human embryonic kidney cell line, with pHelper and pRC using PEI (Polysciences, USA). Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37 □ incubator, collected after 48 hours, and subjected to 3 cycles of freezing and thawing to obtain each crude virus.

In order to confirm the protein expression of the recombinant adeno-associated viruses delivered to the cells, 293T cells, a human embryonic kidney cell line, were respectively treated with crude viruses AAV5-hGAD65, AAV1-rIL-10 and AAV1-rIL-4, and the protein expression was confirmed by Western blot. Specifically, $8 \times 10^5$ 293 T cells were aliquoted into T25 flasks, and each flask was treated with 700 µL of crude viruses on the next day, followed by culturing in a 37 □ incubator. After 48 hours, the cells and the culture media were harvested separately, and the cells were dissolved with a solubilizing agent and the culture media were concentrated with amicon (Merck Millipore, Germany). The prepared samples were treated with the antibodies to GAD65 (Cell signaling, USA), IL-10 (Santa Cruz, USA) and IL-4 (Santa Cruz, USA), respectively, and subjected to Western blot. The results are shown in FIG. 4.

FIG. 4 is a diagram showing the expression of each protein by conducting Western blot analysis of the cell lysates of 293T cell line, a human embryonic kidney cell line, treated with AAV5-hGAD65, AAV1-rIL-10 or AAV1-rIL-4. By confirming that a target protein was expressed in every case, it was confirmed that there was no problem in the structure and property of the recombinant adeno-associated viruses used in the experiment.

In order to confirm that GABA is produced by AAV5-hGAD65, the culture media of the cells treated with AAV5-GAD65 were collected under the same condition as that for sample preparation for Western blot, and subjected to GABA ELISA (LDN, Netherland) analysis. The results are shown in FIG. 5. Two identical samples were prepared separately for each experiment group, and the bar represents the value for each sample. As a result, it was confirmed that GABA was secreted into the culture medium by GAD65 introduced into the cells by AAV5-hGAD65 viruses.

E. Preparation of Recombinant Adeno-Associated Viruses

Recombinant adeno-associated viruses were prepared and purified by KRcrogen (Korea) for animal efficacy experiments, and the preparation method is as follows.

Three types of plasmids (pAAV-hGAD65, pAAV-rIL-10, and pAAV-rIL-4) prepared above were respectively transfected into 293T cells, a human embryonic kidney cell line, using calcium phosphate method with pHelper and pRC. Herein, pRC5 into which the capsid gene of AAV serotype 5 was introduced was used for hGAD65, while pRC1 into which the capsid gene of AAV serotype 1 was introduced was used for rIL-10 and rIL-4. The transfected cells were cultured in a 37 □ incubator, and collected after 48 hours.

Then, only the bands containing viruses were isolated and purified through high-speed centrifugation depending on cesium concentration gradient, to obtain AAV5-hGAD65, AAV1-rIL-10 and AAV1-rIL-4. The titers of the produced viruses were measured using qPCR method established by the manufacturer.

<Example 2> Analgesic Efficacy Test of AAV-IL-10 and AAV-GAD65

A. Preparation of Administration Samples 30 minutes before the animal administration, the recombinant adeno-associated viruses stored at −80 □ were thawed at room temperature within 1 minute and mixed well by vortex. And Coomassie blue dye solution was prepared by mixing 10 mg of Coomassie blue in 1 mL of PBS well, and then filtering by syringe filters. 1 µL of AAV-GAD65 of $5.4 \times 10^5$ VG/µL, 1 µL of AAV-IL-10 of $1.8 \times 10^7$ VG/µL and 1 µL of 0.1% Coomassie blue dye were mixed under the calculation that each animal gets 3 µL in total. The samples were prepared in twice the amount required, and 3 µL of the sample was administered to each animal.

As a control group, Gabapentin was mixed in animals' drinking water 1 hour prior to administration, which was prepared in a concentration of 10 mg/mL.

B. Preparation of Neuropathic Pain Animal Model and Sample Administration

Male SD-rats of 180 to 200 g were anesthetized with inhalation anesthesia, and then upper parts of the calves were incised, and both ends of the common peroneal nerve and tibial nerve were tied and knots were made by 7-0 suture at 0.5-1 cm intervals. The portions of the two nerve bundles between the knots were cut by a scissor and the incision site was sutured. Two weeks later, von Frey filament test was conducted to confirm pain induction, and then the test substance was administered (C. J. Woolf, *Pain* 87, 2000).

The test substance was administered to dorsal root ganglion (DRG). After inhalation anesthesia of the pain animal model, rat's back at the lumbar spine from L3 to L5 was linearly incised to expose vertebral bones, and then a transverse process, one of the spinal projections, was exposed at the side of the exposure, and the L4 process covering the DRG in the fixed state was carefully separated under the Stereo zoom microscopic view by a rongeur such that the DRG is not damaged. The area around the DRG was manipulated so that the DRG which extends in an oblique line was exposed like grains of rice.

A Hamilton syringe was connected to a polyethylene catheter, and 3 µL of the test substance was accurately collected. Then, the syringe was replaced with a 1 mL syringe for the administration. The rats were placed on a small animal stereotaxic instrument, and the sample was injected while confirming that the micro-needle was pricking the L4 a DRG accurately under a surgioscope. Herein, it was confirmed that the sample containing dye did not leak out of the DRG and was well delivered to the inside of the DRG. After confirming that entire sample was delivered to the DRG, the syringe was separated from the DRG, and suturing was conducted, and the animals were recovered.

Gabapentin was orally administered at 3 mg/kg.

C. Observation of Analgesic Efficacy Using Von Frey Filament Test

The 50% up & down threshold method established by Dixon in 1992 was employed since it is a commonly known method. The method calculates threshold values based on the predetermined patterns of pain responses with a total of 8 filaments whose N values were 0.4, 0.6, 1, 2, 4, 6, 8 and 15 g, respectively. Pain developing regions were searched by changing positions from the region of most lateral toe to the heel of the sole where pain developed.

Rats abruptly lift the soles and shrink or lick the soles when pain occurs. Accordingly, when pain developing region was found, the surrounding area was pricked 5 times with the filament of the next step and if there were responses for 3 times or more, it was regarded as a pain response, and the rats were observed with the filament of the next step. The patterns were recorded at every step. The pain patterns were recorded based on the pattern table established by S. R. Chaplan (Quantitative assessment of tactile allodynia in the rat paw. *Journal of Neuroscience Methods*, 1994) and the threshold values were calculated using it. The behavior analysis of the animal groups is conducted by a blind method for 4 to 6 weeks, observed by at least 3 people, and the results of the recorded patterns are statistically processed to analyze the tendency of pain.

The results of pain-observation employing von Frey filament test where the pain animal model was administered with samples are shown in FIG. 6. FIG. 6 shows the results of comparing the efficacies between co-administration of AAV-GAD65 and AAV-IL-10 and administration of gabapentin. When GAD65 and IL-10 were co-administered, statistically significant pain-relieving effect was observed as compared to the untreated control group (negative control), and the effect was found to be higher than that of Gabapentin.

<Example 3> Analgesic Efficacy Tests of AAV-IL-10 and AAV-GAD65

A. Preparation of Administration Samples

For the preparation of administration samples, rAAV5-GAD65 and rAAV1-rIL-10 which were prepared in Example 1 and stored in a frozen state were thawed, and samples were prepared in accordance with substantially the same method as the preparation method of administration samples in Example 2. Specifically, the single administration substance AAV-GAD65 or AAV-rIL-10 and the co-administration substances AAV-GAD65 and AAV-rIL-10 were diluted in PBS in a virus titer-based mixing ratio of 1:1, 1:5, or 1:30 as shown in Table 1, and 1 µL of 0.1% Coomassie blue dye was added to each sample under the calculation that each animal gets 3 µL. The samples were prepared in twice the amount required for the total population, and 3 µL of the sample was administered to each animal.

TABLE 1

| | Virus types and contents | |
|---|---|---|
| Samples | AAV-GAD65 | AAV-IL-10 |
| Comparative Example 1 (GAD alone) | $5.4 \times 10^5$ VG/2 µL | 0 |
| Comparative Example 2 (IL-10 alone) | 0 | $1.8 \times 10^7$ VG/2 µL |
| Experimental Example 1 (1:1) | $5.4 \times 10^5$ VG/1 µL | $5.4 \times 10^5$ VG/1 µL |

TABLE 1-continued

| | Virus types and contents | |
|---|---|---|
| Samples | AAV-GAD65 | AAV-IL-10 |
| Experimental Example 2 (1:5) | $5.4 \times 10^5$ VG/1 µL | $2.7 \times 10^6$ VG/1 µL |
| Experimental Example 3 (1:30) | $5.4 \times 10^5$ VG/1 µL | $1.8 \times 10^7$ VG/1 µL |

B. Observation of Analgesic Efficacy Using Von Frey Filament Test

Samples were administered to the pain animal models prepared by the same method as in Example 2, and pain was observed using a von Frey filament test, and the results are shown in FIG. 7.

FIG. 7 illustrates the efficacies of AAV-GAD65 and AAV-IL-10 depending on composition ratios thereof. Particularly, as compared to trace amounts of AAV-GAD65 and AAV-rIL-10 which showed no analgesic efficacy, the composition ratios showing synergistic efficacies in animal behavior analysis were verified by the experiments with the mixing composition ratios of AAV-rIL-10 to AAV-GAD of 1:1 (Experimental Example 1), 1:5 (Experimental Example 2) and 1:30 (Experimental Example 3). As a result, the co-administration composition of AAV-GAD65 and AAV-rIL-10 according to the present invention showed an increasing pattern of the pain treatment efficacy as the mixing composition ratio of AAV-rIL-10 to AAV-GAD increased.

<Example 4> Analgesic Efficacy Tests of AAV-IL-10 and AAV-GAD65 Using Transforaminal Epidural Injection A. Preparation of Administration Samples 30 minutes before the animal administration experiment, the reagents kept at −80 □ were thawed at room temperature within 1 minute and mixed well by vortex. AAV-GAD65 and AAV-IL-10 were diluted in PBS to obtain the viral titers shown in Table 2. In order to administer 5 µL of the sample to each animal, the two virus diluted solutions were mixed half and half to obtain 1.5 times the volume required. Then, 5 µL of the sample was administered to each animal.

TABLE 2

| | Virus types and contents | |
|---|---|---|
| Samples | AAV-GAD65 | AAV-IL-10 |
| Experimental Example1 (1:10) | $5.0 \times 10^6$ VG/2.5 µL | $5.0 \times 10^7$ VG/2.5 µL |
| Experimental Example2 (1:30) | $5.0 \times 10^6$ VG/2.5 µL | $1.5 \times 10^8$ VG/2.5 µL |

B. Preparation of Neuropathic Pain Model and Sample Administration

The neuropathic pain animal model was prepared by the same method as described in Example 2, and then the test substance was administered. The test substance was administered by transforaminal epidural administration method at a position adjacent to the dorsal root ganglion (DRG). After inhalation anesthesia of the neuropathic pain animal model, rat's back at the lumbar spine from L3 to L5 was linearly incised to expose vertebral bones, and then, L4 transverse process, one of the spinal projections, was exposed at the side of the exposure. The rat was laid down sideways such that its side aspect could be seen from above, so that the L4 intervertebral foramen was visible.

A micro needle attached to the catheter was put into the prepared sample. A Hamilton syringe was connected to the opposite end of the catheter and pulled until reaching the marking of 5 µL to inject the sample into the catheter. After removing the Hamilton syringe from the catheter, the portion 1 cm apart from the tip of the needle was gripped by Halsted-Mosquito. As L4 spine was gripped by a forcep and pulled upward, the tip area of the needle fixed by Halsted-Mosquito Straight was placed around the L4 intervertebral foramen. The tip of the needle was inserted into the intervertebral foramen whose space had been secured, and advanced until the needle reached a bent portion inside the intervertebral foramen, and the needle which had been gripped was released. After confirming that the needle was fixed, a 1 mL syringe was connected to the polyethylene catheter connected at the opposite side to the needle. The piston was gently pressed to slowly administer the diluted administration substance to the area around the rat' DRG, followed by suturing, to complete the administration procedure. By the same method as described in Example 2, pain results employing the von Frey filament test were observed at 4 weeks after administration of the substance. The results are shown in FIG. 8.

FIG. 8 shows that a mixture of AAV-GAD65 and AAV-IL-10 exhibits efficacy even when administered by the transforaminal epidural administration method. In addition, synergistic efficacy in animal behavior analysis was confirmed at the mixed composition ratios of AAV-GAD65 to AAV-IL-10 of 1:10 (Experimental Example 1) and 1:30 (Experimental Example 2).

<Example 5> Comparison of Efficacies of AAV-GAD65 and AAV-IL-10 with AAV-GAD65 and AAV-IL-4

A pain animal model was prepared by substantially the same method as in Example 2, and the preparation procedure of the administration sample was the same as well. AAV1-rIL-4 described in Example 1 was thawed and prepared for use in animal experiments as follows.

30 minutes before animal's DRG administration experiment, the reagents stored at −80 □ were thawed at room temperature within 1 minute and mixed well by vortex. 10 mg of Coomassie blue was mixed well in 1 mL of PBS, and then, dyes filtered by syringe filters were prepared. AAV-GAD65 and AAV-rIL-4 were diluted in PBS to obtain the virus titer-based mixing ratios shown in Table 3, and 1 µL of 0.1% Coomassie blue dye was added to each sample under the calculation that each animal gets 3 µL. The samples were prepared in twice the amount required for the total population, and 3 µL of the sample was administered to each animal.

The pain results employing the von Frey filament test were observed, and the results are shown in FIG. 9. The FIG. 9 shows the results of comparing the efficacies of AAV-GAD65 and AAV-rIL-10 with AAV-GAD65 and AAV-rIL-4, which illustrates the synergistic efficacies comparatively which appeared in animal behavior analysis when IL-10 and IL-4, cytokines having anti-inflammatory effects, were used in combination with GAD65, respectively. As shown in FIG. 9, the pain treatment efficacy was insignificant or not observed when GAD65, IL-10 or IL-4 was administered alone, and no significant analgesic efficacy was observed when GAD65 and IL-4 were co-administered as compared to the cases where GAD65 or IL-4 was administered alone. On the other hand, when GAD65 and IL-10 were co-administered, it was confirmed that there was higher analgesic efficacy which was statistically significant as compared to the other comparative examples. In particular, synergistic pain-relieving effect was observed, which was not shown when GAD65 and IL-4 were co-administered.

<Example 6> Preparation and Characterization of Recombinant Adeno-Associated Virus A. Construction of pAAV-Flag-hGAD65

The pAAV-Flag-hGAD65 was constructed by adding the Flag sequence to pAAV-GAD65 prepared in Example 1.A.

```
Flag sequence (SEQ ID NO: 26):
GATTACAAGGATGACGACGATAAG
```

The Flag sequence was added to modified pAAV-GAD65 by the same method. The modified pAAV-GAD65 was prepared as follows.

After pAAV-GAD65 was cut with NheI, an arbitrary random base sequence (SEQ ID NO: 27) was inserted between the CMV promoter and the GAD65 gene by an infusion method using primers of SEQ ID NOS: 28 and 29. The base sequences used for the insertion are as follows.

```
Scramble stuffer (SEQ ID NO: 27):
5'-GTCGACGGTATCGATAAGCTTGATATCGAATTCCTGCAGCCC-3'

Forward primer (SEQ ID NO: 28):
5'-CTAGGTCGACGGTATCGATAAGCTTGATATCGAATTCCTGCAGCC
C-3'

Reverse primer (SEQ ID NO: 29):
5'-CTAGGGGCTGCAGGAATTCGATATCAAGCTTATCGATACCGTCGA
C-3'
```

Next, the WPRE base sequence (Schambach, Gene Ther, 2006) from which the X-protein region that can amplify the oncogenic effect was removed was amplified by PCR, and inserted downstream of the GAD65 gene using PacI and

TABLE 3

| Samples | Virus types and contents | | |
| --- | --- | --- | --- |
| | AAV-GAD65 | AAV-IL-10 | AAV-IL-4 |
| Comparative Example 1 | 5.0 × 10⁵ VG/2 µL | — | — |
| Comparative Example 2 | — | 1.8 × 10⁷ VG/2 µL | — |
| Comparative Example 3 | — | — | 1.8 × 10⁷ VG/2 µL |
| Comparative Example 4 | 5.4 × 10⁵ VG/1 µL | — | 1.8 × 10⁷ VG/1 µL |
| Experimental Example 1 | 5.4 × 10⁵ VG/1 µL | 1.8 × 10⁷ VG/1 µL | — |

HpaI restriction enzymes. At the same time, a portion of SV40 pA was removed to prepare modified SV40 pA. The primer sequences used for WPRE amplification are as follows.

Forward primer (SEQ ID NO: 30):
5'-GGTGGTTTAATTAAAATCAACCTCTGGATTACAAAATTTG-3'

Reverse primer (SEQ ID NO: 31):
5'-GGTGGTFGTTAACGACAACACCACGGAATTG-3'

B. Construction of pAAV-hGDNF/hIL-10

The pVAX1 (Invitrogen) was added with human IL-10 and the human GDNF gene by the same method as in Example 1 to prepare pAAV-GDNF-IL-10. The IL-10 gene was synthesized using the gene represented by the sequence of NCBI NM_012854 by referring to Bioneer. The human GDNF gene was synthesized using the gene represented by the sequence of NCBI NM_ 199231.2 by referring to Bioneer.

C. Preparation and Characterization of Recombinant Adeno-Associated Virus

The adeno-associated viruses used in the experiment are AAV serotype 5 containing human GAD65 or human GAD65 added with Flag, and AAV serotype 5 containing human GDNF/human IL-10. Each adeno-associated virus was produced from the plasmid DNA prepared in Examples 6A and 6B by referring to a production site, and the information on the viruses used in each experiment and the production sites are shown in Table 4 below.

TABLE 4

| | Virus types | Production sites | Notes |
|---|---|---|---|
| 1 | AAV5-GAD65 | NCH | Used in Example 14 |
| 2 | AAV5-Flag-GAD65 | SCT, Cdmogen | Used in Examples 9, 10 |
| 3 | AAV5-Flag-GAD65 | Cdmogen | Used in Example 13 |
| 4 | AAV5-GDNF/IL-10 | Cdmogen, NCH | Used in Examples 10, 14 |

The cell lysates of HeLa cell line treated with the AAV5-GAD65 or AAV5-Flag-GAD65 virus produced above were treated with GAD65 (Millipore, USA) or Flag (Cell signaling, USA) antibodies respectively to conduct Western blotting, and the results are shown in 10A to 10D. Also, GDNF ELISA (R & D systems, USA) and IL-10 ELISA (R & D systems, USA) were conducted using HeLa cell culture solutions treated with AAV5-GDNF/IL-10 virus. The results are shown in FIG. 10E.

The above results showed that target proteins were expressed, indicating that there was no problem in the structures and property of the recombinant adeno-associated viruses used in the experiment <Example 7> Construction of Recombinant Adenovirus The recombinant Ad-GFP virus manufactured and sold by Cdmogen was used. It was verified that there is no problem in the structure and property of the recombinant Ad-GFP virus by the manufacturer's result report when it was purchased.

<Example 8> Construction and Characterization of pAAV-GFP Plasmid

The hrGFP was added to pAAV-rIL10 prepared in Example 1, to construct pAAV-GFP. Specifically, pAAV-rIL10 was treated with Nhe1 and Pac1 to remove rIL10. Next, the hrGFP gene region was amplified by PCR. The primer sequence used in PCR is as follows.

Forward primer (SEQ ID NO: 32):
5'-GGT GGT GCT AGC GCC ACC ATG GTG AGC AAG CAG ATC CT-3'

Reverse primer (SEQ ID NO: 33):
5'-GGT GGT TTA ATT AAC ACC CAC TCG TGC AGG CT-3'

The hrGFP fragments obtained by treating hrGFP with Nhe1 and Pac1 were ligated to construct pAAV-GFP.

FIG. 11 shows the result of observing GFP protein expression by fluorescence microscopy after treating 293T cell line, a human embryonic kidney cell line, with pAAV-GFP using jetprime (Polyplus, France). The above results showed that target proteins were expressed, indicating that there was no problem in the structures and property of the recombinant adeno-associated viruses used in the experiment <Example 9> Examination of Delivery to Nerve Tissue and Cytotoxicity of Recombinant Adeno-Associated Virus after Administration to a DRG Using Rat Animal Model In order to find out whether the recombinant adeno-associated virus is delivered to the nerve tissue when administered to a DRG, $1 \times 10^9$ VG/2 μL of AAV5-Flag-hGAD65 produced in Example 6 and 1 μl of 0.1% Coomassie blue dye were administered to the animals of the rat animal model at 3 μL per/rat by the same method as in Example 2. The test substances were administered to a DRG by the same method as in Example 2. One week after the administration of the test substances, the DRG, a site for administration, was removed, and gDNA was extracted, and then qPCR was conducted with primers and probes capable of detecting the test substances in the extracted gDNA. The results of qPCR are shown in Table 5 below.

TABLE 5

| Group | L4 (left) DRG region (vector genomic copies/μg) |
|---|---|
| Vehicle | Negative |
| AAV5-Flag-hGAD65 | 121,472 |

In order to find out whether the recombinant adeno-associated virus shows cytotoxicity to the nerve tissue when administered to a DRG, $1.08 \times 10^9$ VG/2 μL of AAV5-Flag-hGAD65 produced in Example 6 and 1 μl of 0.1% Coomassie blue dye were administered to the animals by the same method as in Example 2. The test substances were administered to a DRG by the same method as in Example 2. After administration of the test substances, a DRG, a site for administration, was removed, and gDNA was extracted, and then histopathological examination with hematoxylin & eosin (H & E) staining was conducted to determine whether the test substances exhibited nerve cell cytotoxicity (FIG. 12)

In the control group and the administration group, axonal degeneration, Schwann cell proliferation, and foamy/vacuolated/pigmented macrophages were observed, which were determined to be caused by physical damages from direct stimulation of administration rather than changes generated by the test substance. Therefore, it was found that the recombinant adeno-associated virus was delivered to the nerve tissue effectively, but showed slight cytotoxicity when the virus was administered to a DRG.

<Example 10> Examination of Delivery to Nerve Tissue and Cytotoxicity of Recombinant Adeno-Associated Virus by Transforaminal Epidural Injection Using Rat Animal Model In order to find out whether the recombinant adeno-associated virus is delivered to the nerve tissue by transforaminal epidural injection, $1 \times 10^9$ VG/2.5 µL of AAV5-hGDNF/hIL-10 or $2 \times 10^9$ VG/5 µL of AAV5-Flag-hGAD65 produced in Example 6 were administered to the animals of the rat animal model by the same method as in Example 4. The transforaminal epidural administration of the test substances were conducted by the same method as in Example 4. One week after administration of the test substance AAV5-hGDNF/hIL-10, a DRG, a site for administration, was removed, and gDNA was extracted, and then qPCR was conducted with primers and probes capable of detecting the test substances in the extracted gDNA.

The results of qPCR are shown in Table 6 below.

TABLE 6

| Group | L4(left) DRG region (vector genomic copies/µg) |
|---|---|
| Vehicle | Negative |
| AAV5-hGDNF/hIL-10 | 145,446 |

4 weeks after administration of the test substance AAV5-Flag-hGAD65, a DRG, a site for administration, was removed, and immunohistochemical staining was conducted to examine delivery of the recombinant adeno-associated virus to the DRG and the presence or absence of nerve cell infection (FIG. 13A).

In order to find out whether the recombinant adeno-associated virus shows cytotoxicity to the nerve tissue by transforaminal epidural administration, $1.08 \times 10^9$ VG/5 µL of AAV5-hGAD65 produced in Example 6 was administered to the animals of the rat animal model by the same method as in Example 4. The transforaminal epidural administration was conducted by the same method as in Example 4. After administration of the test substance, a DRG, a site for administration, was removed, and histopathological examination with hematoxylin & eosin (H & E) staining was conducted to determine whether the test substances exhibited nerve cell cytotoxicity (FIG. 13B)

Nerve cell damage was not observed in the control and treatment groups. However, infiltration of very few mononuclear cells and polymorphonuclear leukocytes was observed in the capsule of the nerve fiber. But due to the very small number of the infiltrating cells, it was not considered to be significantly different from the case in which no infiltration was observed. Therefore, it was found that the recombinant adeno-associated virus was delivered to the nerve tissue effectively, and showed no cytotoxicity when the virus was administered by transforaminal epidural injection.

<Example 11> Examination of Delivery to Nerve Tissue of Recombinant Adenovirus by Transforaminal Epidural Injection Using Rat Animal Model In order to find out whether the recombinant adeno virus is delivered to the nerve tissue by transforaminal epidural injection, Ad-GFP $1 \times 10^{10}$ virus particles/5 µL produced in Example 7 were administered to the animals of the rat animal model by the same method as in Example 4. The transforaminal epidural administration of the test substances was conducted by the same method as in Example 4. One day after administration of the test substance, a DRG, a site for administration, was removed, and then immunohistochemical staining was conducted to examine delivery of the recombinant adeno virus to the DRG and the presence or absence of nerve cell infection (FIG. 14). It was found that the recombinant adeno virus was delivered to the nerve tissue effectively by transforaminal epidural injection.

<Example 12> Examination of Delivery to Nerve Tissue of Plasmids by Transforaminal Epidural Injection of Plasmid Using Rat Animal Model In order to find out whether the plasmids are delivered to the nerve tissue by transforaminal epidural injection, 5 µg/5 µL of the pAAV-GFP plasmid produced in Example 8 were administered to the animals of the rat animal model by the same method as in Example 4. The transforaminal epidural administration of the test substances was conducted by the same method as in Example 4. One day after administration of the test substance, a DRG, a site for administration, was removed, and then immunohistochemical staining was conducted to examine delivery of the plasmids to the DRG and the protein expression of the delivered gene (FIG. 15). It was found that the plasmids were delivered to the nerve tissue effectively by transforaminal epidural injection.

<Example 13> Examination of Delivery to Nerve Tissue of Recombinant Adeno-Associated Virus by Transforaminal Epidural Injection Using Dog Animal Model In order to find out whether the recombinant adeno-associated virus is delivered to the nerve tissue by transforaminal epidural injection, AAV5-Flag-hGAD65 produced in Example 6 was administered to the 4 sites of L4 and L5 DRG at a dose of $2 \times 10^{12}$ VG/100 µL each, with a total dose of $8 \times 10^{12}$ VG/400 µL in a dog animal model.

Using a 21-gauge spinal needle under the guidance of a real-time fluoroscope (C-arm fluoroscopic X-ray system (Zen-7000, Zenoray, South Korea)), an injection needle was inserted at the position 3 cm lateral to the position in the middle of the two lumbar spinous processes, toward the inferior portion of an articular process, at an angle of 30 to 45 degrees on a sagittal plane. If the tip of the needle contacted the vertebral body or spinous process, its direction was changed and the needle was inserted close to the entrance of the intervertebral foremen. To avoid nerve roots emerging from the spinal cord, the needle was proceeded under the X-ray guidance toward a target point, the inferior portion of the accessory process of the caudal vertebral notch. The final position of the needle tip under the real-time fluoroscope was set at the base of the pedicle, at the lateral edge of the vertebral body near the intervertebral foramen. Then, it was confirmed that blood or cerebrospinal fluid did not come out by aspiration. Then 0.1 ml of a water-soluble iodinated contrast medium (Omnipaque 300; GE Healthcare, Seoul, Korea) was injected through a spinal needle to examine its spreading pattern around the nerve ganglion. Under the C-arm imaging, DPBS or the test substance was slowly injected around the DRG in the L4 and L5 intervertebral foramen (total 4 sites) at 0.1 ml per site (FIG. 16).

Two weeks after administration of the test substances, the DRG was removed and gDNA was extracted. And then qPCR was conducted with primers and probes capable of detecting the test substances in the extracted gDNA.

The results of qPCR are shown in Table 7 below.

TABLE 7

| Group | DRG qPCR results (vector genomic copies/μg) | |
|---|---|---|
|  | Left L4 | Left L5 |
| Vehicle | Negative | Negative |
| AAV5-Flag-hGAD65 | 560,550 | 105,894 |

<Example 14> Examination of Delivery to Nerve Tissue of Recombinant Adeno-Associated Virus by Transforaminal Epidural Injection Using Micro-Pig Animal Model In order to find out whether the recombinant adeno-associated virus is delivered to the nerve tissue by transforaminal epidural injection, AAV5-hGAD65 and AAV5-hGDNF/hIL-10 produced in Example 6 were mixed in a ratio of 1:1 and administered to the 2 sites of left L4 and L5 DRG at a dose of $1\times10^{12}$ VG/200 μL each, with a total dose of $2\times10^{12}$ VG/400 μL.

Under the guidance of a real-time fluoroscope (C-arm fluoroscopic X-ray system (Zen-7000, Zenoray, South Korea)), the number of lumbar vertebrae was examined, and all subjects were administered at the DRG of L4 and L5 levels irrespective of the number of lumbar vertebrae. Using a spinal needle (23G×3, ½", 0.60×90 mm, Taechang Industry, Korea), the injection needle was inserted at the position about 1.5 cm lateral to the upper edge of the lumbar spinal process, toward the region where the lateral surface of the vertebral body and the inferior edge of the transverse process meet, in a caudal direction at an angle of 30 to 45 degrees on a sagittal plane. Under the X-ray guidance, the target point of the needle for transcutaneous and lumbar transforaminal epidural injection was set to the cranial ¼ point in the intervertebral foramen between L4 and L5. If the tip of the needle contacted the transverse process, its direction was changed to the caudal direction, and the needle was inserted close to the entrance of the intervertebral foramen through the lower edge of the transversal process. In order to avoid nerve roots emerging from the spinal cord, the needle was proceeded directly under the vertebral pedicle, lower lateral to the pars interarticularis, toward the upper portion of the intervertebral foramen.

The final position of the needle tip under the real-time fluoroscope was set to the base of the pedicle, at the lateral edge of the vertebral body near the intervertebral foramen. When an abnormal sensation was felt during the insertion process, the needle was moved backward by several millimeters and the tip of the needle was placed at a position where no abnormal sensation was felt, and it was confirmed that blood or cerebrospinal fluid did not come out by aspiration. Then 0.3 ml of a water-soluble iodinated contrast medium (Omnipaque 300; GE Healthcare, Seoul, Korea) was injected through a spinal needle to examine its spreading pattern around the nerve ganglion, which was video-recorded. Thereafter, under the C-arm imaging, test substances were injected slowly around the DRG in the left L4 and L5 intervertebral foramen at 0.2 ml per injection site (FIG. 17).

Three weeks after administration of the test substances, a DRG was removed and gDNA was extracted. And then qPCR was conducted with primers and probes capable of detecting the test substances in the extracted gDNA.

The results of qPCR are shown in Table 8 below.

TABLE 8

| Group | DRG qPCR results (vector genomic copies/μg) | |
|---|---|---|
|  | Left L4 | Left L5 |
| Vehicle | Negative | Negative |
| AAV5-hGAD65 + AAV5-hGDNF/hIL-10 | 36,830 | 66,676 |

The invention claimed is:

1. A method for delivery of a biological molecule to a nervous tissue, which comprises injecting the biological molecule into a space between inside of an intervertebral foramen and dura mater surrounding spinal cord and spinal nerve,
  wherein the biological molecule is a nucleic acid; and
  wherein the nervous tissue is a dorsal root ganglion or a spinal nerve.

2. The method of claim 1, wherein the intervertebral foramen is a space between a body of vertebra and a vertebral arch through which a spinal nerve emerges from the spinal cord.

3. The method of claim 1, wherein the nucleic acid is in the form of RNA or DNA.

4. The method of claim 3, wherein the RNA is in the form of mRNA, miRNA, siRNA or shRNA.

5. The method of claim 4, wherein the mRNA encodes an active protein.

6. The method of claim 4, wherein the miRNA, siRNA or shRNA has a sequence complementary to a nucleic acid encoding a target protein.

7. The method of claim 3, wherein the DNA encodes an active protein or shRNA.

8. The method of claim 3, wherein the DNA is loaded in a vector.

9. The method of claim 8, wherein the vector is a viral vector, a plasmid, a cosmid, a bacterial artificial chromosome, a yeast artificial chromosome, or a human artificial chromosome.

10. The method of claim 9, wherein the viral vector is any one selected from the group consisting of adenovirus, adeno-associated virus, herpesvirus, lentivirus, retrovirus, poxvirus, and a combination thereof.

* * * * *